US 6,670,038 B2

(12) United States Patent
Sun et al.

(10) Patent No.: US 6,670,038 B2
(45) Date of Patent: Dec. 30, 2003

(54) METHOD OF DEPOSITING PARTICLES WITH AN ELECTROSTATIC CHUCK

(75) Inventors: Hoi Cheong Steve Sun, Dayton, NJ (US); Timothy Allen Pletcher, Eastampton, NJ (US)

(73) Assignee: Delsys Pharmaceutical, Monmouth Junction, NJ (US)

( * ) Notice: Subject to any disclaimer, the term of this patent is extended or adjusted under 35 U.S.C. 154(b) by 0 days.

(21) Appl. No.: 10/174,301

(22) Filed: Jun. 17, 2002

(65) Prior Publication Data

US 2003/0087023 A1 May 8, 2003

Related U.S. Application Data

(63) Continuation of application No. 09/740,123, filed on Dec. 19, 2000, now Pat. No. 6,440,486, which is a continuation of application No. 09/175,287, filed on Oct. 20, 1998, now Pat. No. 6,294,024, which is a continuation-in-part of application No. 08/661,210, filed on Jun. 10, 1996, now Pat. No. 5,858,099, which is a continuation-in-part of application No. 08/630,050, filed on Apr. 9, 1996, now Pat. No. 5,846,595.

(51) Int. Cl.[7] .............................. B32B 5/16; A61K 9/14; A61K 9/20
(52) U.S. Cl. .................... 428/403; 424/464; 424/474; 424/490; 427/181; 427/197; 427/472; 427/474
(58) Field of Search .................. 428/403; 427/181, 427/197, 212, 469, 472, 474; 424/464, 474, 490

(56) References Cited

U.S. PATENT DOCUMENTS

| | | | |
|---|---|---|---|
| 3,798,048 A | 3/1974 | Brody et al. ............... 118/640 |
| 4,072,129 A | 2/1978 | Bright et al. | |
| 4,160,257 A | 7/1979 | Carrish | |
| 4,197,289 A | 4/1980 | Sturzenegger et al. | |

(List continued on next page.)

FOREIGN PATENT DOCUMENTS

| | | |
|---|---|---|
| GB | 2253164 | 2/1992 |
| JP | 57-196211 | 2/1982 |
| JP | 08-080453 | 3/1996 |

OTHER PUBLICATIONS

Daviet, et al., "Electrostatic Clamping Applied to Semiconductor Plasma Processing, I. Theoretical Modeling", J. Electrochem. Soc., vol. 140, No. 11, pp. 3245–3256, Nov. 1993.

(List continued on next page.)

*Primary Examiner*—H. Thi Le
(74) *Attorney, Agent, or Firm*—Dechert LLP

(57) ABSTRACT

The present invention is directed to electrostatic chucks, methods for their use, the electrostatic deposition of objects, such as particles in a dry powder, onto recipient substrates, and the recipient substrates themselves that have been subjected to electrostatic deposition. In one aspect, the present invention provides an electrostatic chuck for electrostatically attracting an object or objects wherein the object is used in chemical or pharmaceutical assaying or manufacturing. The objects can be pharmaceutical substrates, for example, such as a pharmaceutical tablet. Additional embodiments of the invention provide chucks and their use to electrostatically attract particles, such as a pharmaceutically active ingredient, to a substrate, such as a tablet. In one aspect, the electrostatic chuck comprises a floating electrode, and is used to selectively attract particles to a substrate above the floating electrode, thereby providing for charge imaging for the deposition of particles in a selected image. Additionally, the invention provides comprising a sensing electrode, optionally for use with an electrostatic chuck, for sensing the number of particles attracted to the objects on the chuck or other substrate, thereby providing for deposition of an accurate amount of particles. Furthermore, the present invention provides objects having selected areas in which particles are applied to the object via electrostatic means.

12 Claims, 11 Drawing Sheets

U.S. PATENT DOCUMENTS

| | | | |
|---|---|---|---|
| 4,332,789 A | | 6/1982 | Mlodozeniec |
| 4,349,531 A | | 9/1982 | Mlodozeniec et al. |
| 4,502,094 A | | 2/1985 | Lewin et al. |
| 4,554,611 A | | 11/1985 | Lewin |
| 4,652,318 A | | 3/1987 | Masuda et al. |
| 4,685,620 A | | 8/1987 | Law |
| 4,795,644 A | | 1/1989 | Zentner |
| 4,860,417 A | | 8/1989 | Tajima et al. |
| 4,917,978 A | | 4/1990 | Ritt et al. |
| 4,921,727 A | | 5/1990 | Datta et al. |
| 4,921,767 A | | 5/1990 | Datta et al. |
| 4,971,257 A | | 11/1990 | Birge |
| 5,028,501 A | | 7/1991 | Ritt et al. |
| 5,278,588 A | | 1/1994 | Kubelik |
| 5,377,071 A | | 12/1994 | Moslehi |
| 5,463,525 A | | 10/1995 | Barnes et al. |
| 5,522,131 A | | 6/1996 | Steger |
| 5,534,309 A | | 7/1996 | Liu |
| 5,619,984 A | | 4/1997 | Hodson et al. |
| 5,642,727 A | | 7/1997 | Datta et al. |
| 5,647,347 A | | 7/1997 | Van Oort |
| 5,698,269 A | | 12/1997 | Carlblom et al. |
| 5,846,595 A | | 12/1998 | Sun et al. |
| 5,858,099 A | | 1/1999 | Sun et al. |
| 6,303,143 B1 | * | 10/2001 | Chrai et al. |
| 6,326,149 B1 | * | 12/2001 | Loewy et al. |
| 6,440,486 B2 | * | 8/2002 | Sun et al. |
| 6,511,712 B1 | * | 1/2003 | Poliniak et al. |

OTHER PUBLICATIONS

Daviet, et al., "Electrostatic Clamping Applied to Semiconductor Plasma Processing, II. Experimental Results", J. Electrochem. Soc., vol. 140, No. 11, pp. 3256–3261, Nov. 1993.

Field, "Electrostatic Wafer Clamping For Next Generation Manufacturing", Solid State Technology, pp. 91–98, Sep. 1994.

Harstough, "Electrostatic Wafer Holding", Solid State Technology, pp. 87–90, Jan. 1993.

Nakasuji, et al., "Low Voltage and High Speed Operating Electrostatic Wafer Chuck Using Sputtered Tantalum Oxide Membrane", J. Vac. Sc. Technol. A., 12, 5, pp. 2834–2839, Sep./Oct., 1994.

Singer, "Electrostatic Chucks in Wafer Processing", Semiconductor International, pp. 57–64, Apr. 1995.

Watanabe, et al., "Electrostatic Force and Absorption Current of Alumina Electrostatic Chuck", J. Appl. Phys. vol. 31, pp. 2145–2150, 1992.

Watanabe, et al., "Electrostatic Charge Distribution in the Dieletric Layer of Alumina Electrostatic Chuck", Journal of Materials Science, vol. 29, pp. 3510–3616, 1994.

Copy of International Search Report dated Jul. 16, 1997, from corresponding International Application No. PCT/US97/05352.

* cited by examiner

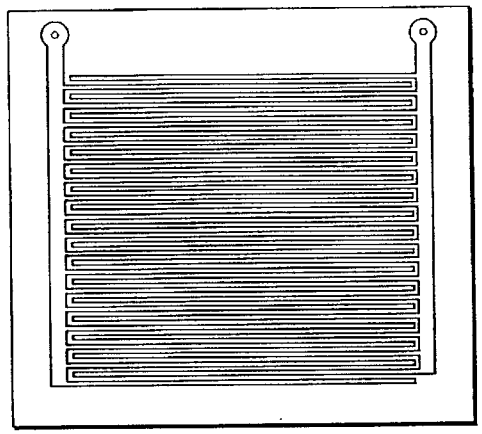
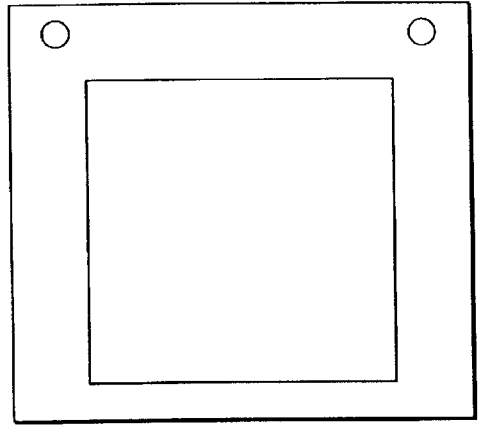
FIG. 16A    FIG. 16B
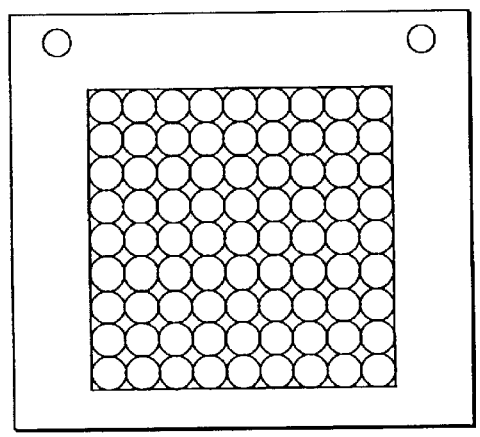
FIG. 16C

METHOD OF DEPOSITING PARTICLES WITH AN ELECTROSTATIC CHUCK

This application is a Continuation Application of U.S. Ser. No. 09/740,123, filed Dec. 19, 2000 now U.S. Pat. No. 6,440,486, which is a Continuation of Ser. No. 09/175,287, filed Oct. 20, 1998, now U.S. Pat. No. 6,294,024, which is a Continuation-in-part of Ser. No. 08/661,210, filed Jun. 10, 1996, now U.S. Pat. No. 5,858,099, which is a Continuation-in-part of Ser. No. 08/630,050, filed Apr. 9, 1996, now U.S. Pat. No. 5,846,595.

U.S. Pat. Nos. 5,871,010 ("Inhaler Apparatus with Modified Surfaces for Enhanced Release of Dry Powders), U.S. Pat. No. 5,857,456 ("Inhaler Apparatus with an Electronic Means for Enhanced Release of Dry Powders"), U.S. Pat. No. 5,753,302 ("Acoustic Dispenser"), U.S. Pat. No. 5,788,814 ("Chucks and Methods for Positioning Multiple Objects on a Substrate"), U.S. Pat. No. 5,714,007 ("Apparatus for Electronically Depositing a Medicament Powder Upon Predefined Regions of a Substrate"), U.S. Pat. No. 6,007,630 ("Method and Apparatus for Electrostatically Depositing a Medicament Powder Upon Predefined Regions of a Substrate"), U.S. Pat. No. 5,669,973 ("Apparatus for Electrostatically Depositing and Retaining Materials Upon a Substrate") and U.S. Pat. No. 5,642,727 ("Inhaler Apparatus Using a Tribo-Electric Charging Technique"), describe, among other things, the electrostatic deposition of objects, such as particles of powder, on a substrate. The foregoing patent applications are hereby incorporated herein by reference, in their entirety.

The present invention is directed to electrostatic chucks, methods for their use including the electrostatic deposition of particles on an objects, and the objects themselves that have been subjected to electrostatic deposition. In one aspect, the present invention provides an electrostatic chuck for electrostatically attracting an object or objects wherein the object is used in chemical or pharmaceutical assaying or manufacturing. The objects can be pharmaceutical substrates, for example, such as a pharmaceutical tablet or an inhaler substrate.

Additional embodiments of the invention provide chucks and their use to electrostatically attract particles, such as a pharmaceutically active ingredient, to a substrate, such as a tablet. In one aspect, the electrostatic chuck comprises a floating electrode, and is used to selectively attract particles to a substrate above the floating electrode, thereby providing for charge imaging for the deposition of particles in a selected image. Additionally, the invention provides an electrostatic chuck comprising a sensing electrode for sensing the number of particles attracted to the chuck, thereby providing for deposition of an accurate amount of particles. Furthermore, the present invention provides objects having selected areas in which particles are applied to the object via electrostatic means.

In the pharmaceutical industry, pharmaceutical compositions with an active ingredient are prepared by mechanically mixing the active ingredient with pharmaceutically acceptable carriers. A major drawback to this method is the inaccuracy of distribution of the active ingredient in the individual tablets of a batch. This problem is particularly evident when the active ingredient is present in a low dosage, and the inaccuracy of mechanical mixing can result in individual tablets in a single batch having different dosages.

Additionally, for example, some pharmaceutical compositions contain a mixture of various carriers together with the active ingredient in which the carrier is not fully compatible with the active ingredient. For example, the active ingredient may be poorly soluble in the carrier or the carrier may negatively affect the bioavailability of the active ingredient.

These drawbacks of the prior art are addressed by the present invention, in which electrostatic chucks are provided together with their use in the pharmaceutical or chemical industries, providing for accurate deposition of an active ingredient on a tablet, among other advantages.

SUMMARY OF THE INVENTION

The disadvantages heretofore associated with the prior art are overcome by inventive technique and apparatus for holding an object or multiple objects, such as tablets, without the use of mechanical force, for deposition of a pharmaceutically active ingredient, for example. The present invention provides advantages including cost-effectiveness, efficiency, and, for example, greater accuracy in the application of a specified pharmaceutical dosage to a pharmaceutical substrate such as a tablet. Further, the deposition of a pharmaceutically active ingredient using static electricity is particularly useful, for example, when the active ingredient is immiscible or otherwise incompatible with the remainder of the tablet or other substrate.

In one aspect, the present invention provides an electrostatic chuck comprising a conductive layer having at least one electrode for electrostatically attracting an object wherein the object is used in chemical or pharmaceutical assaying or manufacturing. For example, the object can be coated with a pharmaceutically active compound. The objects can be numerous types of substrates, including, for example, objects that are suitable for human consumption. The objects can be pharmaceutical substrates, such as an inhaler substrate, a pharmaceutical tablet, capsule, caplet, suppository, dressing, bandage and a patch. In certain embodiments, the pharmaceutical substrate is not dielectric.

Certain embodiments provide the use of an electrostatic chuck to electrostatically attract objects, such as particles, to a recipient substrate. "Particles" are defined herein as objects having a size less than about one millimeter in width or diameter. Thus, the electrostatic chucks of the invention can be used, for example, to attract particles of a powder having a pharmaceutically active ingredient to a recipient pharmaceutical substrate, which substrate may be pharmaceutically inert.

Another aspect of the present invention provides the use of an electrostatic chuck to attract an object wherein the thickness of the object is preferably less than about 5 mm, and more preferably, less 20 than about 3 mm.

In one embodiment of the invention, the electrostatic chuck has two electrodes in the upper conductive layer exposed to the objects, and the two electrodes are preferably interdigitated. In other embodiments, the chuck has a single electrode in the upper conductive layer. The chuck can be used, for example, to hold an object against gravitational forces, or, for example, to position multiple objects on a substrate. See, for example, U.S. Pat. No. 5,788,814.

Certain aspects of the invention provide an electrostatic chuck comprising a floating electrode, wherein the chuck is used to selectively attract objects, such as particles, to a substrate above the floating electrode, thereby providing for charge imaging for the deposition of particles in a selected image. Additionally, the invention provides a sensing electrode for sensing the number of objects, such as particles, that have been deposited onto a recipient substrate. In certain preferred embodiments, a sensing electrode is located on an electrostatic chuck. The sensing electrode provides for deposition of an accurate amount of objects, such as particles. The particles deposited on the recipient substrate can include, for example, a pharmaceutically active ingredient.

Furthermore, the present invention provides objects having selected areas in which particles are applied to the object via electrostatic means.

Additionally, in one aspect, the present invention provides an electrostatic chuck comprising an inhaler substrate, the substrate comprising a conductive layer having at least one electrode for electrostatically attracting particles for inhalation. Preferably, the particles comprise particles of a dry powder comprising a pharmaceutically active ingredient.

The present invention additionally provides methods using an electrostatic chuck. For example, the invention provides a method of chemical or pharmaceutical manufacturing comprising:

(a) providing an electrostatic chuck; and
(b) electrostatically attracting an object to the chuck, wherein the object is used in chemical or pharmaceutical manufacturing.

In addition to a method of manufacturing, the present invention provides the use of an electrostatic chuck to electrostatically attract an object to a substrate wherein the object is a support for a chemical reaction used in a chemical assay or to manufacture chemicals or pharmaceuticals.

The invention also provides the use of an electrostatic chuck to electrostatically attract one object or multiple objects to a substrate wherein the thickness of the object is less than about 3 mm. Additionally, the invention provides for the use of an electrostatic chuck having a bias potential for attracting an object to a substrate, the bias potential being less than the breakdown potential of the materials forming the chuck.

The methods of the present invention can be used with numerous objects including an edible substrate, a pharmaceutical substrate, such as an inhaler substrate, a tablet, capsule, caplet, suppository, dressing, bandage and a patch, and optionally when the substrate is not dielectric. Additionally, the methods of the invention can be used with particles that include a pharmaceutically active ingredient, and the methods of the invention include their use to coat an object, such as a tablet, with a pharmaceutically active compound.

Further, the invention provides a method of attracting a selected number of particles to a substrate, comprising:

(a) providing an electrostatic chuck with a sensing electrode;
(b) applying multiple electrostatically charged particles to the chuck; and
(c) sensing the number of particles attracted to the chuck. This method can be used, for example, with particles of a dry powder wherein the method is used to determine the amount of powder deposited on a substrate attracted to the chuck.

Another aspect of the invention provides a method of depositing particles onto selected areas of a substrate, the method comprising the use of an electrostatic chuck with floating electrodes in areas of the chuck that correspond to the selected areas of the substrate. Additionally, the invention provides a method of manufacturing a pharmaceutical composition comprising (a) providing a pharmaceutical substrate; and (b) electrostatically depositing particles on the substrate, the deposition preferably comprising the use of an electrostatic chuck. Preferably, the electrostatic chuck comprises a floating electrode and the particles are substantially deposited on an area of the substrate corresponding to the floating electrode, and the electrostatic chuck preferably further comprises a sensing electrode for determining the amount of particles deposited on the substrate.

In another aspect, the present invention provides a method for producing a dosage form comprising: (a) providing an electrostatic chuck having an area that is x- or y-addressable; (b) contacting the chuck with objects comprising a pharmaceutically active ingredient, wherein the objects substantially adhere to the chuck in the areas that are x- or y-addressable; and (c) releasing the objects onto a pharmaceutical carrier aligned with the areas of the chuck on which the objects are adhered. Preferably, the chuck has multiple areas that are x- or y-addressable, each area corresponding to a separate pharmaceutical carrier. Further, the objects are preferably substantially simultaneously deposited onto multiple pharmaceutical carriers. This method can be used, for example, to form different dosage units, when at least two of the pharmaceutical carriers receive a different number of objects. This method is particularly convenient for pharmaceutically active ingredients such as hormones that are administered in varying dosages, and it is desirable to form a pharmaceutical package containing more than one type of dosage unit.

BRIEF DESCRIPTION OF THE DRAWINGS

FIGS. 16A–C provide three photographs of an electrostatic chuck according to the present invention. FIG. 16A shows the electrostatic chuck circuit; FIG. 16B shows a window mask for the chuck and FIG. 16C shows the chuck assembly with an array of tablets.

DETAILED DESCRIPTION OF THE INVENTION

Figure 1:
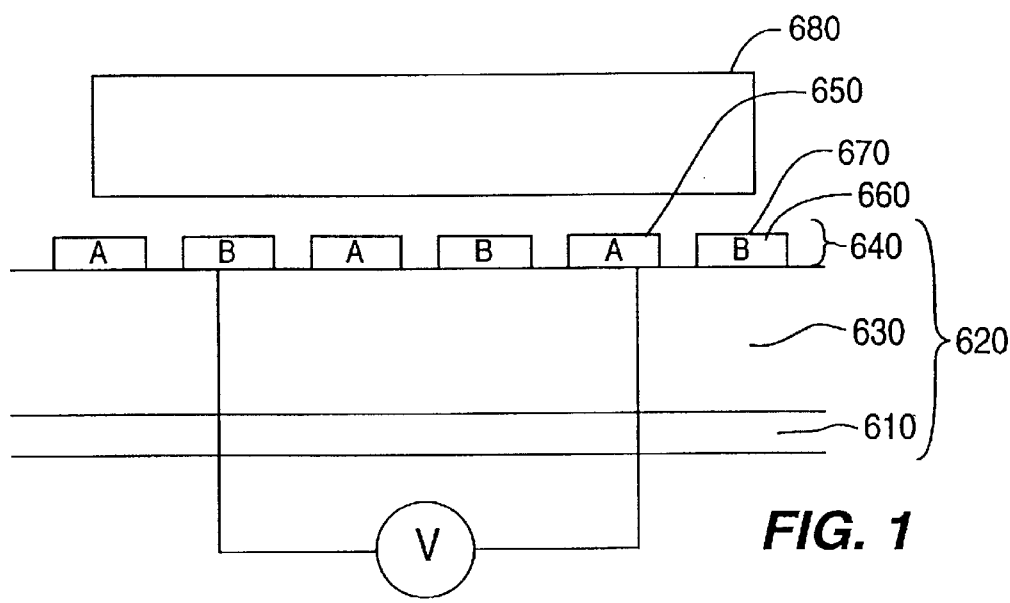
FIG. 1 is a cross-sectional view of a schematic representation of an electrostatic chuck with interdigitated electrodes according to the present invention.

For purposes of this application, the following terms have the indicated meanings.

Acoustic dispenser: an apparatus for dispensing particles that employs vibration having a frequency in the acoustic (audible) range.

Chuck: a clamp for holding an object or objects.

Chuck for positioning objects: a chuck having a configuration that can be used for substantially arranging objects on the chuck in a selected pattern.

Electrostatic chuck: a clamp for holding an object or objects using electrostatic force.

Electrostatic chuck with conductive vias: an electrostatic chuck for positioning objects, in which the chuck has a layer that determines the positioning of the objects, and this layer has vias containing a conductive material.

Mechanical Chuck: a chuck that uses compression to hold an object.

Non-Mechanical Chuck: a chuck that does not use compression to hold an object, including but not limited to a chuck that uses electrostatic or vacuum (i.e., negative pressure) means for such holding.

Object: a material thing.

Particle: an object equal to or less than about one millimeter in width or diameter.

Pitch: the repeat distance between the edge of one well to the corresponding edge of the adjacent well in, for example, a microtiter plate.

Recipient substrate: an object having a surface or layer that is coated with or will receive a coating of objects, such as particles.

Upper conductive layer: the conductive layer of an electrostatic chuck that attracts or adheres objects to the chuck.

1. Uses of the Electrostatic Chucks of the Invention

"Chucks" are defined above as clamps for holding an object or objects. Instead of using conventional clamps that employ mechanical or compressive force, the present invention is directed to the use of static electricity in an electrostatic chuck as the means used by the context of the chuck to hold objects. The objects can optionally be positioned, transported and deposited. Preferably, the chucks use a force other than positive pressure for holding objects. The chucks of the present invention can be used, in one aspect, for positioning objects, which is described in U.S. Pat. No. 5,788,814 ("Chucks and Methods for Positioning Multiple Objects on a Substrate.")

In one aspect, the present invention provides electrostatic chucks for electrostatically attracting an object or multiple objects. Without being limited to any particular theory, it is believed that when an electric potential is applied to the electrostatic chucks of the invention, capacitors are formed between the electrodes of the chuck and objects are held by the electrostatic force. One of the advantages of using an electrostatic chuck in the chemical or pharmaceutical industry is that, unlike plasma charging, electrostatic charging (also known as tribocharging) generally does not negatively affect chemicals. Further, the use of an electrostatic chuck provides the ability to hold a pharmaceutical substrate, for example, without requiring mechanical force that could disrupt the substrate.

The chucks of the present invention can be used to hold an object or multiple objects against gravitational forces during chemical or pharmaceutical processing. Additionally, the present invention provides methods of chemical manufacturing using a chuck to attract an object or multiple objects to a substrate, the objects being used in chemical manufacturing. In another aspect, the present invention provides methods of manufacturing a pharmaceutical composition by using a chuck to attract an object or multiple objects to a substrate, the objects being used to manufacture the pharmaceutical composition. The chuck can be manufactured to have an increased size in order to attract an object having an increased surface area.

In one aspect, the present invention provides for the use of an electrostatic chuck having a bias potential for attracting an object or objects to a substrate. Preferably, the bias potential is greater than about 1000 volts. The use of the chuck according to the present invention provides for the possibility of a bias potential since a bias potential does not necessarily cause damage to, for example, a pharmaceutical substrate, unlike a wafer in the semiconductor industry, which is voltage sensitive.

When using an electrostatic chuck, preferably the temperature is between about −50° C. to about 200° C., and preferably from about 22° C. to about 60° C. The humidity is preferably between 0-100% wherein the humidity does not cause condensation; more preferably, the humidity is about 30%.

The use of the electrostatic chucks of the invention can be scaled up for large scale continuous manufacturing, such as using a sheet of an edible substrate for use with tablets, for example, or a sheet of an inhaler substrate, which can be perforated, for example, into individual tapes for individual inhalers.

The present invention also provides methods for depositing a selected number of objects comprising: (a) providing an electrostatic chuck having an area that is x- or y-addressable; (b) contacting the chuck with objects, wherein the objects substantially adhere to the chuck in the areas that are x- or y-addressable; and (c) releasing the objects onto a recipient substrate aligned with the areas of the chuck on which the objects are adhered. The present invention also provides methods for producing a dosage form comprising:

(a) providing an electrostatic chuck having an area that is x- or y-addressable; (b) contacting the chuck with particles comprising a pharmaceutically active ingredient, wherein the particles substantially adhere to the chuck in the areas that are x- or y-addressable; and (c) releasing the particles onto a pharmaceutical carrier aligned with the areas of the chuck on which the particles are adhered.

Advantages of the present invention include the ability to hold a pharmaceutical substrate without the use of a mechanical means. Thus, for example, the present invention provides an electrostatic mechanism for holding a tablet that is loosely compressed and that would crumble if held by mechanical means or by a vacuum chuck. Additionally, for example, without being held to a particular theory, it is believed that the pharmaceutically acceptable carriers, for example, in tablets are frequently conductive and dissipate their charge within less than about a millisecond. An electrostatic chuck provides an advantage by maintaining its charge whereas a pharmaceutical substrate, for example, would otherwise lose its charge.

The present invention also provides electrostatic chucks that are used to hold an object or multiple objects during processing in the chemical or pharmaceutical industry. Such processing includes the deposition of particles on the objects, such as the deposition of a pharmaceutically active powder on tablets. This is particularly useful, for example, when the active ingredient is incompatible with the remainder of the tablet. Furthermore, more than one type of ingredient, such as two active ingredients, can be coated on an object, such as a tablet. The tablet can be further processed after the particles are deposited on it; for example, the tablet can be coated after deposition. Preferably, the particles are dispensed using an acoustic dispenser, described in U.S. Ser. No. 08/630,049.

Without being limited to a particular theory, the electric potential generated by the electrostatic chucks of the present invention is believed to serve both for holding a conductive object in place, such as a tablet, and for attracting a charged object, such as particles within a powder, onto a recipient substrate. Additionally, the electrostatic chucks of the invention can be used for inhaler substrates. See, for example, co-pending application entitled "Inhaler Apparatus with an Electronic Means for Enhanced Release of Dry Powders," filed simultaneously herewith. See also the section on charge imaging chucks below.

2. Objects Held by Electrostatic Chucks of the Invention

A. Sizes and Types of Objects

Preferably, the thickness of an object held by an electrostatic chuck of the present invention is less than about 300 mm, and more preferably, less than about 100 mm, even more preferably, less than about 50 mm, even more preferably, less than about 25 mm, even more preferably, less than about 10 mm, even more preferably, less than about 5 mm, and most preferably, less than about 3 mm. Thus, in certain preferred embodiments, the object is a small object, such as a particle equal to or less than about one millimeter in average width or diameter. In certain preferred embodiments, the chucks of the invention are used with multiple small objects, preferably having a size from about 5 microns to about 500 microns, and preferably for use in the chemical or pharmaceutical industry. The use of an electrostatic chuck in the chemical and pharmaceutical industries is one of the novelties of the present invention.

In certain preferred embodiments, the objects held by a chuck are pharmaceutical substrates, and the objects are round, such as tablets. Alternatively, for example, the objects are oblong, and can be, for example, capsules or caplets. When the object is a tablet, preferably it has a thickness no greater than about 3 mm. The present invention additionally provides for the use of a chuck to hold an object or objects which, in some embodiments, are coated with particles while being held. In preferred embodiments, the particles are within a powder comprising a pharmaceutically active compound.

Preferably, the powder is in dry micronized form, using for example, an air jet milling process, and the particles are at least about 1 micron in diameter, and preferably from about 1 to about 10 microns, and more preferably about 4 to about 8 microns in diameter. Preferably, the powder is electrostatically charged before application to the chuck, for example, through admixture with beads such as by mechanical shaking.

Additional pharmaceutical substrates include, for example, a suppository, or an edible substrate such as a pharmaceutical tablet, capsule or caplet or a water soluble film such as a hydroxypropyl methyl cellulose resin. Other substrates include dressings, bandages and patches, as well as, for example, a substrate for an inhaler. For example, the inhaler can be a flat, ceramic disk upon which a plurality of medicament dosages are positioned. See, for example, U.S. Pat. No. 5,714,007.

The chucks of the present invention can be used for numerous other types of objects, including but not limited to a thin conductive substrate such as an edible polymeric substrate, which can be used as a substrate for deposition of a pharmaceutically active powder, and the substrate can subsequently be used, for example, to create or coat a tablet. Preferably, excess objects that are not electrostatically adhered to the chuck are removed before transferring the objects to a substrate. To release the objects, the application of voltage can be stopped, or for greater force of removal, the voltage can be reversed.

In addition to pharmaceutical objects or particles, the electrostatic chucks of the present invention can be used to attract any other particle that can be adhered to an electrostatic chuck. Additionally, for example, the chucks can be used to attract and deposit liposomes into capsules for cosmetics.

B. Composition of the Objects Held by the Chucks

Preferably, the tablets to be held by the electrostatic chucks of the invention include a substantial amount of cellulose, preferably greater than about 50% cellulose, more preferably greater than about 60% cellulose, even more preferably greater than about 75% cellulose, even more preferably greater than about 90% cellulose, and most preferably about 95% cellulose. In other embodiments, the tablets include about 65% lactose and about 34% cellulose. In certain embodiments, the tablets include about 80% lactose. Preferably, the tablets do not have an ingredient which would cause them to deviate from being either a good conductor or a good dielectric. For example, with a conductive tablet such as one that is substantially made of cellulose, preferably the tablet does not include dielectric metal oxides such as ferrous or ferric oxide or titanium oxide. Preferably the amount of iron oxide, if present, is less than about 1%. Additionally, the tablet preferably does not include moisture and preferably does not include a substantial amount of a salt such as sodium bicarbonate that becomes conductive with high humidity, thereby making the most efficient operation of the electrostatic chuck affected by humidity.

The tablets may optionally have additional components, including but not limited to sodium starch glycolate and magnesium stearate.

When an edible substrate, having for example, a pharmaceutically active powder deposited onto it, is fused with a tablet, preferably the edible substrate is made of substantially the same component as the tablet, such as cellulose. For example, hydroxypropyl methyl cellulose can be used, such as Edisol M Film M-900 or EM 1100 available from Polymer Films Inc. (Rockville, Conn.).

Preferably, the density of the tablet is such that if it has a diameter of about 5.6 mm, the tablet weighs no more than about 100 mg. If the diameter of the tablet is twice as large, the weight can be proportional to the square of the diameter.

The conductivity of a tablet can be determined by measuring the DC impedance, by placing the tablet in an electrical circuit between a voltage source and a picoammeter. The capacitance of the tablet can be measured by placing the tablet sample in parallel with a Hewlett Packard 4192A Low Frequency Impedance Analyzer set for 1 kHz. The tablets are preferably painted on both sides with a thin layer of conductive silver paint to ensure good electrical contact. Several formulations were tested, and conductivities between $2.4 \times 10^9 \Omega$ and $6.3 \times 10^9 \Omega$ were found. The range of impedance was about $2 \times 10^9 \Omega$ to $23 \times 10^{10} \Omega$. The capacitance was determined to be 0.3 pF to 0.5 pF, which correspond to a charge retention time of 100 $\mu$sec. to 1 msec.

3. Charging of Objects

In certain preferred embodiments, the objects to be applied to the chuck are charged prior to their application. The charge can be, for example, either a plasma charge or an electrostatic charge, depending upon the nature of the object to be applied to the chuck. For instance, when using beads, either a plasma or electrostatic charge can be used since neither causes damage to the bead. For other objects that may be damaged by plasma charging, electrostatic charging is preferably used. In preferred embodiments, the methods include electrostatically charging the object before applying it to the chuck. For details regarding the use of carrier beads for charging, see the continuation-in-part, filed simultaneously herewith, of U.S. Ser. No. 08/630,049, filed Apr. 4, 1996.

4. Configuration of the Chucks

The size of the chuck depends upon the number and size of objects to be attracted using the chuck. For example, a 2 inch by 2 inch chuck can hold about 100 tablets in which each tablet has a diameter of about 5.6 mm. Preferably, the chuck is reusable and can be washed between uses.

When using a chuck of the present invention to hold a recipient substrate, such as a tablet, during deposition of particles, such as a powder containing a pharmaceutically active ingredient, the tablets are preferably closely packed on the chuck so that only the tablets receive the powder, and the chuck itself is not coated with powder. For example, the electrostatic chucks of the invention can be used to hold about eighty-one tablets in a row of nine tablets by a column of nine tablets.

In one aspect, the present invention provides an electrostatic chuck comprising a conductive layer forming at least one electrode for electrostatically attracting multiple objects. In other preferred embodiments, the chuck comprises a conductive layer forming two electrodes, which, in certain embodiments, are serpentine or interdigitated and provide for a higher probability that the area of the two electrodes covered by the same object are the same, therefore objects at different locations of the chuck are held at the same potential. Additionally, the surface area is beneficially inversely proportional to the object to be held by the chuck. For example, in preferred embodiments, the electrode has a larger surface area to electrostatically hold a smaller object. The conductive layer that attracts or adheres objects to the chuck is termed an "upper conductive layer", and this layer is not necessarily the outermost layer of the chuck. For example, the upper conductive layer can have a thin dielectric layer on top of it, between the conductive layer and the objects. Further, the chuck may have more than one conductive layer forming an electrode, although only the conductive layer that attracts or adheres objects to the chuck is termed an "upper conductive layer".

In certain preferred embodiments, the electrostatic chucks are made of solid state materials such as glass or silicon dioxide or other ceramics which impart good dielectric strength and therefore better attraction of objects. The better dielectric strength also provides for a thinner layer, and a lower voltage which increases safety. Further, the materials are well-characterized, durable, mechanically strong and readily available.

A. Electrostatic Chuck with Two Electrodes in the Upper Conductive Layer

Figure 2:
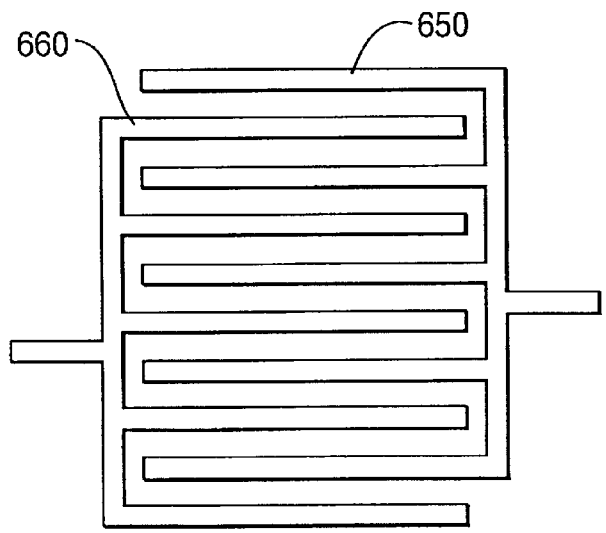
FIG. 2 is a top view of a schematic representation of the interdigitated electrodes of FIG. 6.

Referring to FIG. 1, the lower conductive layer 610 of the chuck 620 is coated with a dielectric layer 630. On top of the dielectric layer is an upper conductive layer 640 forming an interdigitated electrode, with a first electrode 650 and a second electrode 660. A second dielectric layer 670 is placed on top of the upper conductive layer 640. FIG. 2 shows a top view of the two interdigitated electrodes 650 and 660. This chuck 620 can be used to attract an object 680, as shown.

During use of an electrostatic chuck having an upper conductive layer with two interdigitated electrodes, a voltage is applied across the two electrodes of the chuck, preferably about 200 to about 2000 volts. See, for example, Example 4 below. The voltage applied to an electrostatic chuck can be direct current voltage (DC) or alternative current voltage (AC) provided that the same amount of voltage is applied.

B. Mathematical Calculation of the Holding Force of the Chuck

Without being limited to a particular theory, assuming a 1 mm contact area for the tablet, $$\text{Capacitance} = \frac{\varepsilon_0 \varepsilon_r A}{d} = \frac{8.89 \times 10^{-10} \times 1 \times 1 \times 10^{-6}}{50 \times 10^{-6}} \qquad 1$$

$$\approx 17 \, \text{pF}$$

-continued $$E = \frac{1}{2}CV^2$$

$$F = \frac{d\varepsilon}{dX} = \frac{\varepsilon_0\varepsilon_r A V^2}{2X^2}$$

$$\cong \frac{17 \times 10^{-12} \times (500)^2}{2 \times 5^{-0} \times 10^{-6}}$$

$$= 42.5\ \mu N$$

For the capacitor, assuming that X=the thickness of dielectric layer, for a 60 mg tablet, the gravitational force= $60 \times 10^{-6}$ kg×9.8 N/kg=600 $\mu$N and the electrostatic force is therefore about 60 times stronger than the force of gravity.

Without being limited to any particular theory, it is believed that the object need not necessarily have direct physical contact with an electrode in the upper conductive layer in order to be electrostatically held by the chuck. When using the chuck having an upper conductive layer with interdigitated electrodes to deposit a charged powder onto a tablet, for example, the electrostatic force holding the tablet increases as the charged powder is deposited on the tablet, thereby providing an additional advantage in a stronger holding force. There is a limited amount of charged powder that can be deposited using the interdigitated chuck, which is based on bias potential. Therefore, this chuck provides the advantage of the ability to determine the amount of powder deposited upon a substrate by measuring the amount of charge remaining. The charge can be measured using, for example, an electrometer or a picoammeter. The value of the charge can be used to determine the mass of the powder deposited. The design of this chuck provides for its ability to electrostatically hold virtually any object that is conductive relative to the strong dielectric layer on top of the chuck.

Figure 3A:
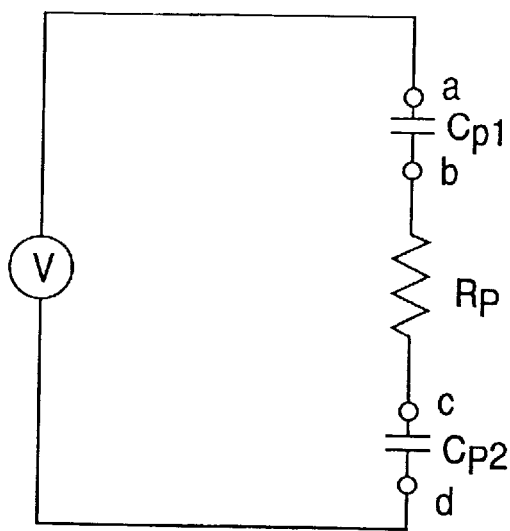
FIGS. 3A and 3B are circuit diagrams of an electrostatic chuck having two electrodes, FIG. 3A depicting the chuck without a lower conductive layer, and FIG. 3B depicting the chuck with a lower conductive layer.
Figure 3B:
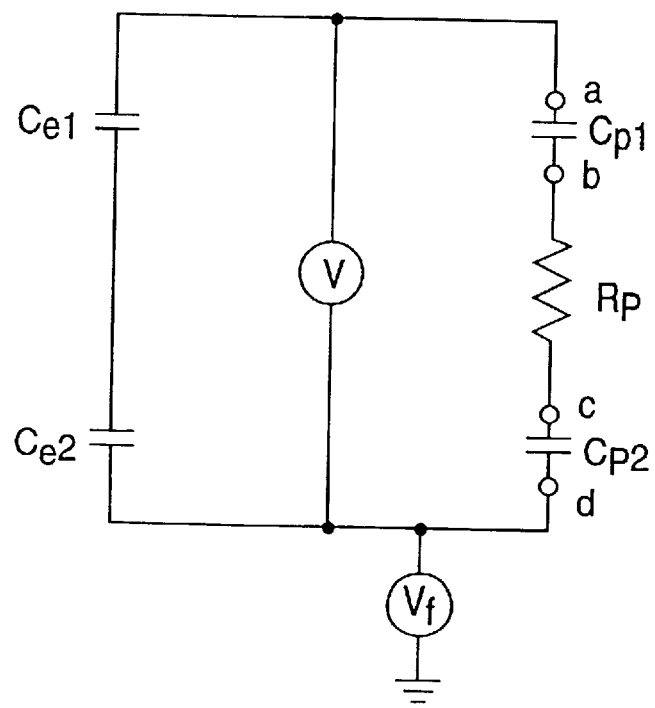

Without being limited to a particular theory, the following mathematical formulas can be used to evaluate the holding force of the electrostatic chuck illustrated in the circuit diagram shown in FIG. 3. FIG. 3A represents a circuit diagram of an electrostatic chuck with an upper conductive layer having two electrodes, each electrode having an object attracted to it, and in which the lower conductive layer is absent. FIG. 3B represents a circuit diagram of a chuck with an upper conductive layer having two electrodes, each electrode having the same object attracted to it, and in which the lower conductive layer is present. $Cp_1$ is the capacitance of the capacitor formed between an object, such as a tablet, and the first electrode; $Cp_2$ is the capacitance of the capacitor formed between an object, such as a tablet, and the second electrode; Rp is the resistance due to the object; and V represents the holding potential which is related to the force holding the object onto the chuck. Referring to FIG. 3B, $Ce_1$ is the capacitance of the capacitor formed between the lower conductive layer and the first electrode; $Ce_2$ is the capacitance of the capacitor formed between the lower conductive layer and the first electrode; and $V_f$ represents the bias potential.

A conductive object and the electrode in the upper conductive layer form a capacitor with a capacitance approximately equal to $$C = \frac{\varepsilon_0 \varepsilon_r A}{d} 2 \tag{1}$$

where $\varepsilon_0$, is the dielectric constant of a vacuum, and $\varepsilon_r$ is the relative dielectric constant of the dielectric layer on top of the electrodes in the upper conductive layer; A is the contact area and d is the thickness of the dielectric layer. The force holding of the conductive object and the electrode in the upper conductive layer is given by:

$$F = \frac{\varepsilon_0 \varepsilon_r A V^2}{2d^2} 3 \tag{2}$$

where V is the voltage across the dielectric layer. Assuming $\varepsilon_r=3$ for a polymer, V=350 V, d=10 $\mu$m and A=15 mm$^2$, the electrostatic force is 0.24 N. If the material has a mass of 60 mg, the gravitational force is 0.59 mN. The electrostatic force is over 400 times stronger than the gravitational force.

In the circuit diagram shown in FIG. 3, $V_{ad}$=V. Provided enough charging time elapsed after the voltage V is applied, $V_{bc}$=O. When charged powders land on $R_p$, the voltage across the two capacitors is rearranged. However, the power supply maintains the overall voltage drop $V_{ad}$ as a constant. In a practical design, $C_{p1}$ is approximately the same as $C_{p2}$ and $V_{ab}$~$V_{cd}$~V/2. The overall attractive force is proportional to $(V_{ab}^2+V_{cd}^2)$~$V^2/2$. If the voltage on point b (or c) is altered due to the landing of the charge powders by V', the new attractive force is proportional to $V^2/2+2V'^2=V^2/4+V'^2$. As a result of the addition of the charged powder, the attractive force increases. Also, normal leakage current through the two capacitors of limited resistance is supplied by the power supply as well.

The applied potential V can be maintained at a separated voltage difference $V_f$ with respect to ground. The potential at the conductive material (in this application, the conductive material is a tablet) is $V_f$+V/2. If the tablet is exposed to a cloud of charged powders, the powders will experience the field due to the potential $V_f$+V/2 and be attracted or repelled according to the sign of the charge on powder. If the resultant force is attractive, the powder will be deposited onto the tablet. Since both $V_f$ and V can be controlled in magnitude as well as the sign, the resultant force can be controlled so that it is attractive for deposition.

Without being limited to any particular theory, it is believed that before any conductive material is attached to the chuck shown in FIG. 1 and in the circuit diagram in FIG. 3, the charges will be concentrated on the edges of the electrodes. There is a relatively weak fringing electric field on the top of the electrostatic chuck. This field may not be strong enough to cause charge redistribution in the tablet for attaching the tablet to the chuck. This limitation is removed by the addition of a lower conductive layer beneath the chuck, also known as a backplane. This conductive layer causes the charges on the electrodes to redistribute more evenly across the electrodes. As a result, a higher fringing electric field on the top of the chuck and a better initial attraction between the tablet and the chuck are formed. The new equivalent circuit is shown in FIG. 3B.

C. Electrostatic Chuck with a Single Electrode in the Upper Conductive Layer

In other preferred embodiments, the chuck comprises an upper conductive layer having a single electrode. Preferably, the chuck includes three layers. The bottom layer is preferably a lower conductive layer made of metal, for example, such as aluminum. Alternatively, for example, the bottom layer can be semiconductive, such as a silicon wafer. The middle layer is a dielectric layer preferably having a high dielectric strength, such as thermally grown silicon dioxide. The top layer is an upper conductive layer forming the electrode, which can extend from the top of the dielectric layer externally, or can be embossed whereby it extends internally into the dielectric layer. The upper conductive layer is made of a conductive material, such as a metal, for example, copper wires, or a semiconductor, for example, polycrystalline silicon. Preferably, the upper conductive layer has no significantly negative effect on a pharmaceutically active compound. In preferred embodiments, the thickness of the upper conductive layer is from about 100 nm to about 500 nm. Preferably, the upper conductive layer comprises conductive stripes, and when used to attract multiple objects, the width of the area between the stripes preferably is approximately equal to the average diameter of the objects, thereby providing for complete coverage of the electrode when the maximum number of objects are held by the chuck. Thus, when the chuck is used to hold objects while particles are being deposited on the objects, this configuration provides for substantially eliminating the deposition onto the chuck itself. See, for example, FIG. 16.

Figure 4A:
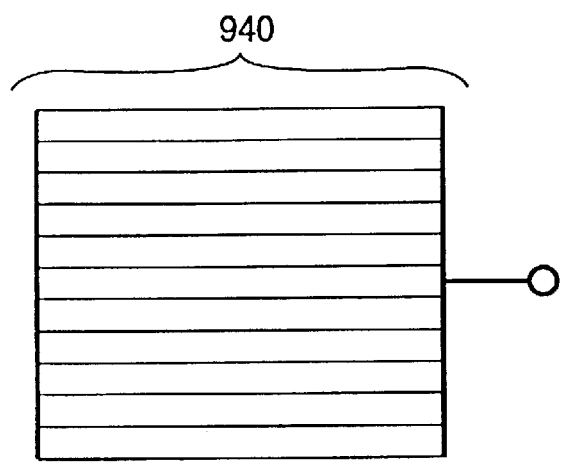
FIG. 4A is a top view of a schematic representation of the single electrode of FIG. 9B.
Figure 4B:
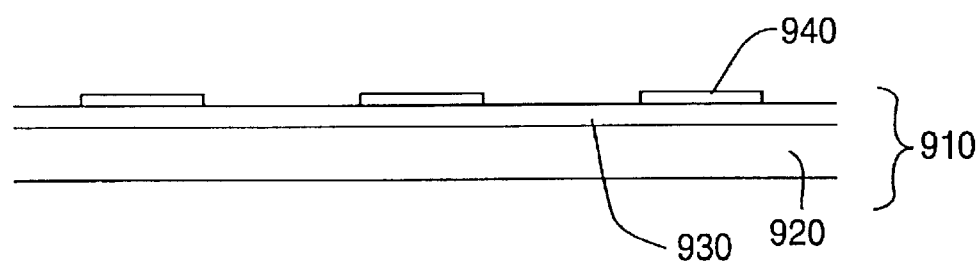
FIG. 4B is a cross-sectional view of a schematic representation of an electrostatic chuck with a single electrode on the upper conductive layer, which protrudes from the dielectric layer, according to the present invention.
Figure 4C:
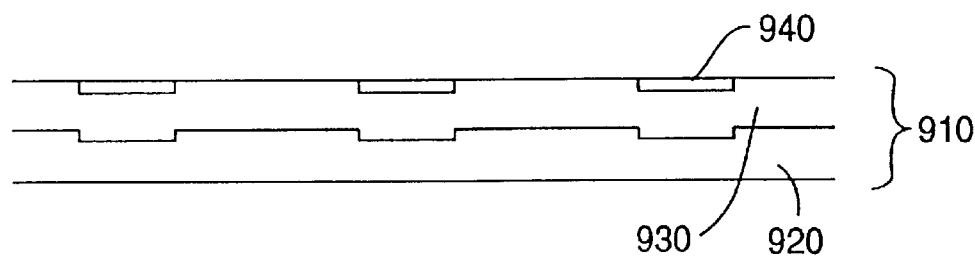
FIG. 4C is a cross-sectional view of a schematic representation of an electrostatic chuck according to the present invention with a single electrode on the upper conductive layer, which is embossed in the dielectric layer.
Figure 6:
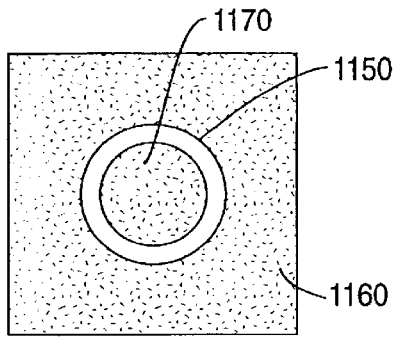
FIG. 6 is a top view of a floating electrode of FIG. 5.
Figure 5:
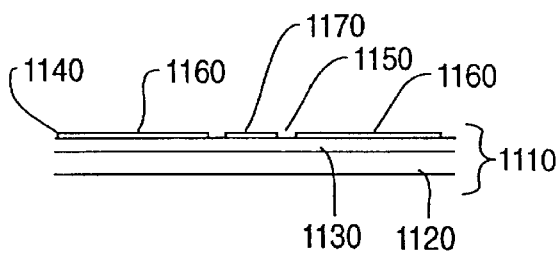
FIG. 5 is a cross-sectional schematic view of an electrostatic chuck with floating electrodes on the upper conductive layer for charge imaging.
Figure 7:
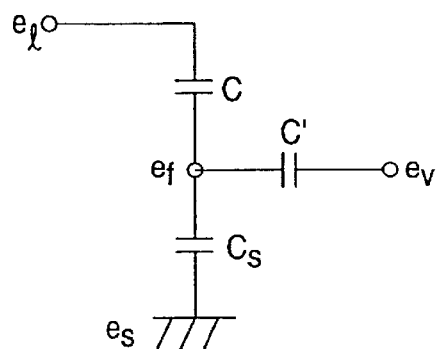
FIG. 7 is a circuit diagram of an electrostatic chuck with a floating electrode on the upper conductive layer.

Referring to FIG. 4B, for example, the electrostatic chuck 910 has a lower conductive layer 920, with a dielectric layer 930 on top of it. The upper conductive layer 940 either protrudes outward from the dielectric layer 930, as shown in FIG. 4B, or is embossed into the dielectric layer 930, as shown in FIG. 4C. A top view of the striations in the upper conductive layer 940 is shown in FIG. 4A. During use of the electrostatic chuck 910, a bias potential is applied between the upper conductive layer 940 and the lower conductive layer 920.

Without being limited to a particular theory, it is believed that when the above-described chuck with a single electrode in the upper conductive layer is used, for example, to electrostatically hold tablets while a charged powder is applied to the tablets, there is no charge redistribution in the tablet, but rather, the tablet is directly charged by contact with the electrode. Therefore, an unlimited amount of charged powder can be deposited on the tablets.

5. X-Y-Addressability of the Chucks and Their Uses

One of the conductive layers, such as the lower conductive layer of the electrostatic chuck, can be made x-addressable or x-y-addressable such that the location of the objects attracted to the chuck can be selected. For example, in an x-addressable chuck, the lower conductive layer has rows in which a single row can be activated at one time. Thus, one can select the placement of objects only on a specific row of the electrostatic chuck, rather than on every row or of the chuck. In an x-y-addressable chuck, the area of the lower conductive layer corresponding each row and column, and therefore, preferably to each object, can be made independent of the remainder of the lower conductive layer corresponding to any of the other rows and columns. Thus, for example, one can select the placement of objects only on specific areas of the electrostatic chuck, rather than throughout the chuck.

Further, the present invention provides an electrostatic chuck comprising a configuration for depositing a selected number of objects onto a recipient substrate. Preferably, the objects are less than about 3 mm in thickness, and the configuration of the chuck preferably comprises a conductive layer having an x or y-addressable area for depositing a selected number of objects onto the recipient substrate. Preferably, the chuck has multiple areas that are x- or y-addressable, each area preferably corresponding to a separate substrate such as a pharmaceutical carrier. In preferred embodiments, the objects are deposited substantially simultaneously onto multiple substrates, and in certain embodiments, the substrates are connected. For example, the substrates can be a pharmaceutical carrier and the objects can be, for example, particles in a powder, microspheres or liposomes which contain a pharmaceutically active ingredient, and together they create a pharmaceutical dosage form. When the substrates are connected, a multidosage pack can be formed in which the dosage decreases, for example, from one unit to the next, such as with a multi-dosage pack for birth control. The dosage can be determined by the number of objects placed into each pharmaceutical carrier using an electrostatic chuck. Thus, the present invention provides a multidosage form having units in which each unit has a dosage, at least two units having different dosages, the dosages being determined by the number of microspheres in the unit. In certain preferred embodiments, the average diameter of the microspheres is from about 1 to about 500 microns, in some instances, preferably about 100 to 500 microns, and in other instances, preferably about 50 microns.

Figure 15:
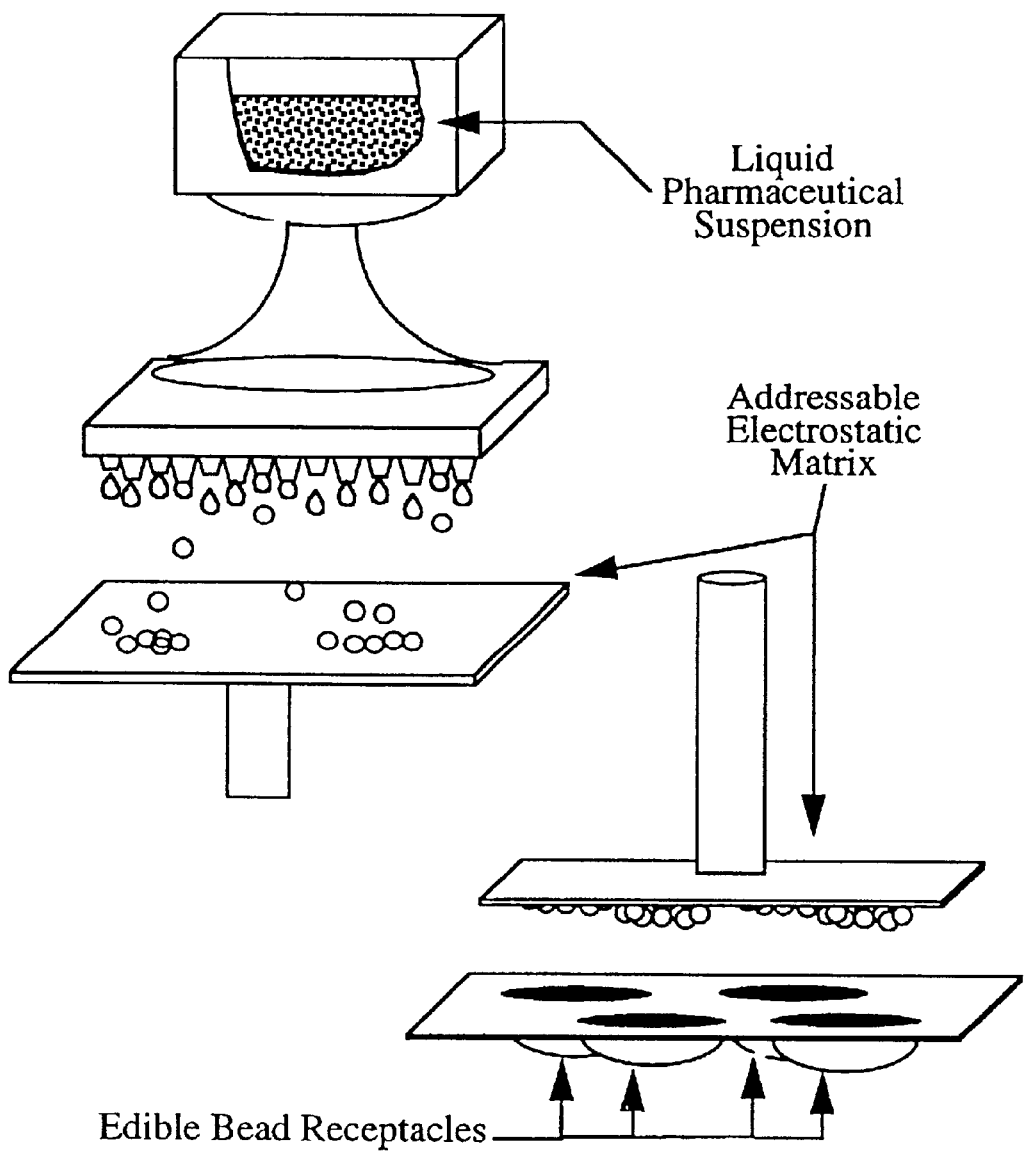
FIG. 15 is a schematic diagram of an electrostatic chuck of the present invention for creating multi-dosage units.

Preferably, the microspheres comprise a pharmaceutically acceptable polyalkylene, such as polyethylene glycol, which is preferably at a concentration of at least about 90%, and more preferably, about 95% polyethylene glycol. The chucks described herein such as for attracting tablets, for example, and for creating charge images, with another dielectric layer, can be used for creating the above described multidosage forms. See, for example, FIG. 15.

6. Charge Imaging Electrostatic Chucks with Floating Electrodes

In further preferred embodiments, electrostatic chucks of the invention are provided for use in charge imaging. Specifically, such an electrostatic chuck comprises a floating electrode for charge imaging. An electrostatic chuck for charge imaging comprises three layers, preferably with an optional fourth layer. The bottom layer is the lower conductive layer, which is also known as the backing electrode. The second layer, on top of the lower conductive layer, is a dielectric layer. The third layer is an upper conductive layer on top of the dielectric layer, and this upper conductive layer has two types of electrodes, floating electrodes and shielding electrodes. In preferred embodiments, the floating electrodes are electrically isolated from the other conductors, and there is a gap between the floating and shielding electrodes. The fourth (optional) layer, on top of the upper conductive layer, is a dielectric layer, which is preferably the layer having contact with the medicament powder. Without being limited to a particular theory, it is believed that when a potential is applied across the shielding and backing electrodes, a charge redistribution occurs on the floating electrodes. This charge redistribution causes electrostatically charged objects to be attracted to the areas of the chuck corresponding to the floating electrodes, thus resulting in deposition in these areas. Preferably, there is a high fringing field in the gap between the floating and shielding electrodes, but this field is preferably not large enough to cause electrical discharge.

The lower conductive layer can be made, for example, of metal, such as silver, copper or aluminized polypropylene, and is preferably about 500 nm in thickness. The dielectric layer can be made of, for example, polyimide, polypropylene, or a semiconductive layer, such as a ceramic, for example, $SiO_2$, such as a thermally grown silicon dioxide, and is preferably about 0.5 to about 2 mils thick. The upper conductive layer is preferably made of a metal, such as silver. Preferably, the upper conductive layer is made of a material that does not negatively affect pharmaceutically active materials.

The upper conductive layer can be made of, for example, a thin gold film coating, and preferably, the floating and shielding electrodes have the same thickness, which is preferably about 500 nm. In preferred embodiments, the gap between the floating electrode and the shielding electrode is from about 25 microns to about 500 microns. The shape of the floating electrode can be varied, and can be irregular, so long as the gap between the floating electrode and the shielding electrode remains substantially constant. In certain preferred embodiments, the floating electrode is round, and forms a dot that can be used to create a selected pattern. In certain preferred embodiments, the shielding electrode is grounded. The shielding electrode is biased with respect to the lower conductive layer. The polarity of the bias is preferably opposite of the powder to be deposited on the substrate.

The fourth layer, on top of the upper conductive layer, is an optional thin dielectric layer, which is preferably made of polyimide or another material of high dielectric strength, and preferably has a thickness of about 10 microns to about 50 microns.

The floating electrodes of the charge imaging chuck determine the pattern of deposition of the medicament powder on the substrate, and hold the powder thereon. During the deposition of powder, the charge imaging chuck is electrically connected to a power source, which is subsequently disconnected after deposition. The floating electrodes can be configured, for example, to spatially determine individual dosages on a substrate. Such substrates include, for example, a tablet and an inhaler substrate.

In preferred embodiments for charge imaging, the floating electrodes are used to selectively attract particles to a substrate in contact with the floating electrodes. Preferably, the substrate has physical contact with the floating electrodes. Without being limited to a particular theory, it is believed that the use of floating electrodes on the electrostatic chuck generates an image of charges by capacitive coupling. Each floating electrode has a charge which is shifted as charged particles contact the electrode. The process of deposition of charged particles on the floating electrode continues until the floating electrode can no longer shift potential, at the point in which it has the same potential as the shielding electrode.

Referring to FIG. 5, for example, the chuck 1110 has a lower conductive layer 1120, with a dielectric layer 1130 on top of it. The dielectric layer has an upper conductive layer 1140 on top of it. The upper conductive layer 1140 is electrically connected, but with a gap 1150 between a shielding electrode 1160 and a floating electrode 1170. A top view of the upper conductive layer 1140 is shown in FIG. 6, with the floating electrode 1170 in the center, and a gap 1150 between the floating electrode and the surrounding shielding electrode 1160. The area of the lower conductive layer 1120 corresponding to each floating electrode can be made addressable in rows, like the x-addressable chucking system described above, or individually addressable, like the x-y-addressable chucking system described above.

During use, a bias potential is applied between the shielding electrode and the lower conductive layer. If the particles to be deposited are positively charged, the bias potential will be negative, and if the particles to be deposited are negatively charged, the bias potential will be positive. Preferably, the shielding electrode is connected to ground. During deposition of particles, the length of time of the deposition will preferably be continued until each and every floating electrode has reached its limit in which the potential of the floating electrode matches the potential of the shielding electrode.

Using an electrostatic chuck with floating electrodes to deposit powder onto a substrate, the amount of powder deposited on the substrate is determined by the charge or bias potential of the chuck, and only a finite amount of powder can be deposited. Without being limited to a particular theory, it is believed that the deposition of powder ends when the charges on the floating electrode can no longer be redistributed, which occurs when the shielding electrode and the floating electrode have substantially the same potential. Preferably, both the floating and shielding electrodes will be at ground potential when the deposition is complete. The amount of powder to be deposited can therefore be controlled by controlling the bias potential, and it is unrelated to the duration of deposition, once the limit has been reached. Furthermore, the pattern of deposition is determined by the pattern of the floating electrodes, which creates a charge image.

For example, a chuck can be used for charge imaging on a substrate to determine the deposition of particles in a particular pattern on the substrate. In preferred embodiments, particles of a powder having a pharmaceutically active ingredient are deposited in a selected pattern onto a recipient pharmaceutical substrate. In certain preferred embodiments, the recipient substrate is a thin dielectric material, such as polypropylene or another thin edible substrate such as hydroxypropyl methyl cellulose, preferably having a thickness of about 25 microns.

Alternatively, for example, an electrostatic charge imaging chuck with a floating electrode can be used to form an inhaler substrate, and to determine the electrostatic deposition of dry powder, for example, onto the substrate. The charge imaging chuck can be used, for example, to determine the spatial location of individual dosages on a substrate. Additionally, the conductive layer of the electrostatic chuck in the inhaler substrate can be used for electronically assisted release of the powder, as described in co-pending application entitled "Inhaler Apparatus with an Electronic Means for Enhanced Release of Dry Powders," filed simultaneously herewith.

Further, the charge imaging chuck can be used outside the pharmaceutical industry, such as for the determination of the deposition pattern of a candy coating on a food item. The electrostatic charge imaging chucks of the invention can be used to hold objects, for example, for the application of a design, such as a candy coating on an edible substrate. Alternatively, for example, the electrostatic charge imaging chucks can be used to hold objects for the application of a dry powder paint.

Without being limited to a particular theory, the following mathematical formulas can be used to evaluate the amount of powder that can be held by the electrostatic chuck having a floating electrode, which is illustrated in the circuit diagram provided in FIG. 7. Referring to FIG. 7, C is the capacitance of the capacitor formed between the lower conductive layer e, and the floating electrode $e_f$. Cs is the stray capacitance of the capacitor formed between the floating electrode $e_f$ and the lower conductive layer $e_l$. C' is the capacitance of the capacitor formed between the floating electrode $e_f$ and the virtual electrode $e_v$, which is formed by the deposited charged powders. The potential of the floating electrode $e_f$ can only be some value between those of the shielding electrode $e_s$ and the lower conductive layer $e_l$, the shielding electrode $e_s$ being grounded in the circuit diagram shown in FIG. 7.

The maximum charge that the floating electrode can hold depends on the bias potential and the capacitor C according to the equation $Q_{max}=CV$. If the fringing field is ignored in order to calculate the maximum charge, the following equation applies:

$$Q_{max} = CV = \frac{\varepsilon_0 \varepsilon_r A}{d} V4$$

where A is the surface area of the floating electrode and d is the thickness of the dielectric layer between the floating electrode and the shielding electrode.

Because $C_s$ is very small compared to C, the deposited charge Q' is approximately equal to Q. The mass M of the deposited powder will be as follows:

$$M = \frac{Q_{max}}{\mu} \cong \frac{\varepsilon_0 \varepsilon_r A}{d} \frac{m}{q} V5$$

where $\mu$ is the charge over mass ratio of the charged powder. By way of example, if $\epsilon_r=2$, d=50 $\mu$m, the diameter of floating electrode=4 mm, $\mu$=50 $\mu$C/g, and V=8 kV, M will be 1.2 mg. Thus, the maximum mass of powder expected to be deposited under these conditions will be 1.2 mg.

Since $C_s \ll C$, $Q'=C'V' \approx Q$.

Therefore, the maximum amount of changed powder is provided by the following equation:

$$\frac{Q'}{\mu} \approx \frac{\varepsilon_0 \varepsilon_r A}{d} \frac{m}{q} V6$$

In addition to providing electrostatic chucks, the present invention also provides methods of charge imaging or depositing particles onto selected areas of a substrate, the method including the use of an electrostatic chuck with floating electrodes in areas of the chuck that correspond to the selected areas of the substrate. Further, the present invention also provides for an object having selected areas in which particles are applied to the object via electrostatic means. In preferred embodiments, the particles comprise a pharmaceutically active ingredient. Preferably, the object is suitable for human consumption. In certain embodiments, the object comprises a pharmaceutical substrate such as an inhaler substrate, a tablet, suppository, dressing, bandage or a patch. Preferably, the amount of particles applied to the object are predetermined using a sensing electrode in the electrostatic chuck.

Advantages of the use of an electrostatic chuck for deposition of particles and for charge imaging include the ability to coat a substrate in a more accurate and more uniform manner, which is particularly important when the dosage of active ingredient is low, such as from about 1 $\mu$g to about 1 mg. Other low dosage ranges include for example, from about 1 $\mu$g to about 500 $\mu$g, and from about 10 $\mu$g to about 250 $\mu$g, and from about 20 $\mu$g to about 100 $\mu$g, such as about 25 $\mu$g. Further, the use of an electrostatic chuck for deposition of particles and for charge imaging provides the advantage, for example, of a mechanism for applying an active ingredient to a pharmaceutical carrier that may be immiscible or otherwise incompatible with the active ingredient.

7. Sensing Electrode for Determining the Amount of Objects Deposited on a Recipient Substrate In addition to providing electrostatic chucks with floating electrodes for charge imaging, the present invention provides chucks with sensing electrodes to sense the amount of charge deposited on a substrate. Furthermore, a single chuck can have both floating and sensing electrodes. In certain aspects of the present invention, the amount of charge that can be deposited on the chuck is limited to a finite number, and this limitation provides a mechanism for accurately determining the amount of powder deposited on the substrate held by the chuck.

In another aspect, the present invention provides an electrostatic chuck having a sensing electrode for sensing the number of particles attracted to the chuck, particularly when the chuck is not self-limiting with respect to the amount of charged particles that can be deposited onto a substrate held by the chuck. The electrostatic chucks, or other surfaces upon which a recipient substrate is located, optionally include sensing electrodes to sense the amount of charge deposited on the recipient substrate. In certain aspects of the present invention, the amount of charge that can be deposited, for example, on an electrostatic chuck is limited to a finite number, and this limitation provides a mechanism for accurately determining the amount of powder deposited on the substrate held by the chuck. Alternatively, the amount of deposition may not be self-limiting. A sensing electrode can be used with an acoustic dispenser, for example, to determine the amount of powder deposited onto a tablet, wherein the powder includes a pharmaceutically active ingredient. Thus, the sensing electrode provides a more accurate and uniform way of dispensing a selected amount of objects. For example, the invention provides for the accurate deposition of a selected amount of a pharmaceutically active ingredient deposited on a substrate, especially when the active ingredient is present in small doses.

The sensing electrode preferably has two layers. The bottom layer is a lower conductive layer forming an electrode made of a metal, for example, such as aluminum. The top layer, which is exposed to the particles being deposited, is a dielectric layer, and is made of a material having a high dielectric strength, such as aluminum oxide. Additionally, for example, the sensing electrode can be made of a thin aluminized polypropylene sheet or a thin polyimide sheet with a copper backing. Without being limited to a particular theory, it is believed that the charged particles land on the dielectric layer and induce an equal and opposite charge on the conductive layer. Due to the presence of the dielectric layer, the possibility of charge neutralization is significantly lowered.

Figure 8:
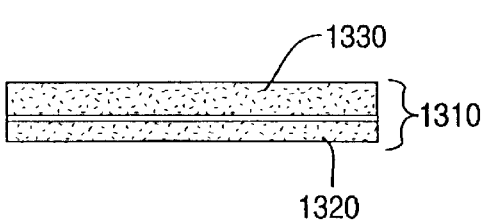
FIG. 8 is a schematic cross-sectional view of a sensing electrode.
Figure 9:
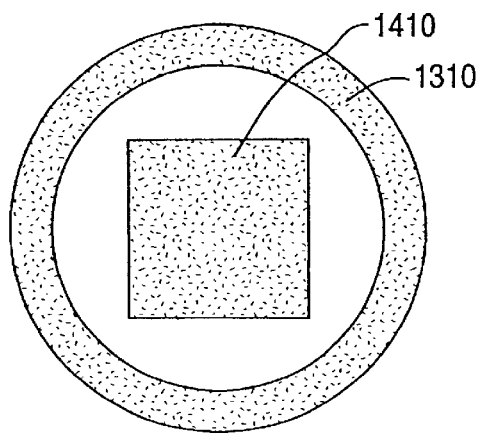
FIG. 9 is a top schematic view of a sensing electrode, with the location of the sensing electrode being outside the area of deposition.
Figure 10A:
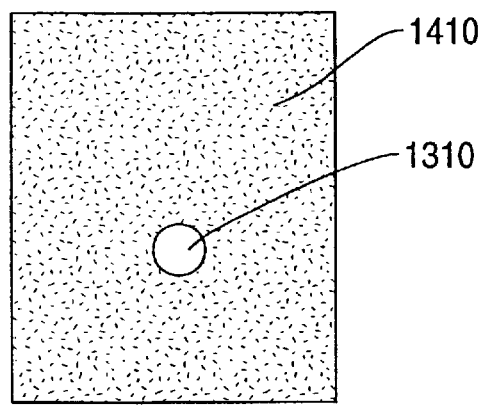
FIG. 10A is a top schematic view of a sensing electrode, with the location of the sensing electrode being inside the area of deposition.
Figure 10B:
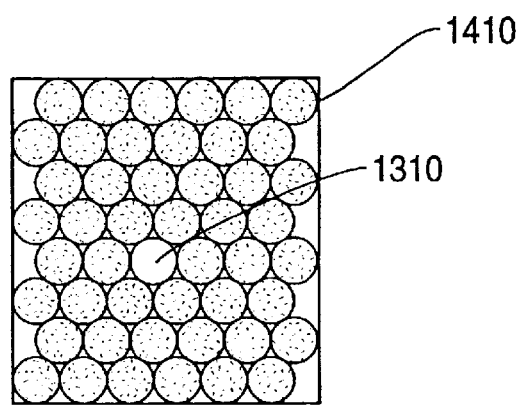
FIG. 10B is a top view of a schematic representation of a sensing electrode, with the location of the sensing electrode in the shape of a tablet, within the area of deposition.

Referring to FIG. 8, for example, the sensing electrode 1310 is constructed of a lower conductive layer 1320 and an upper dielectric layer 1330. As shown in FIG. 9, the sensing electrode 1310 can be placed, for example, in an area outside the substrate 1410 receiving the deposition of particles. In this figure, the sensing electrode 1310 is in the shape of a ring, and other shapes can also be used. The sensing electrode 1310 can also be placed, for example, within the area of the substrate 1410 receiving the deposition of particles as shown in FIG. 10A, when there is a single substrate 1410 receiving deposition. Alternatively, for example, when there are multiple substrates 1410, the sensing electrode 1310 can be placed within the area of deposition, preferably in the shape of one of the substrates 1410 receiving deposition, such as a tablet. Referring to FIG. 10B, for example, the shape of the sensing electrode 1310 mimics the shape of one of the substrates 1410.

The sensing electrode is preferably located in an area that provides for an amount of particles to be deposited on the sensing electrode in direct relation to the amount of deposition on the substrate. More than one sensing electrode can be used with a single substrate. For example, the presence of two sensing electrodes with deposition on a single substrate can be used to determine the relationship between the amount of deposition occurring on the substrate and in areas outside the substrate. The mass of the particles deposited onto the substrate(s) is determined once the charge of the sensing electrode is measured.

Figure 11:
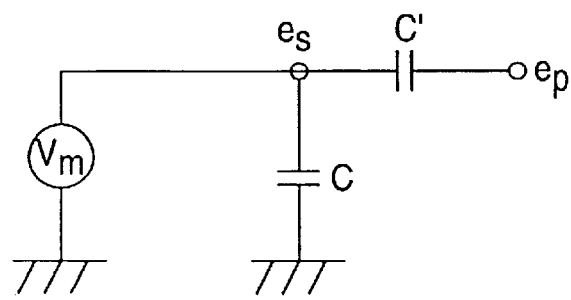
FIG. 11 is a circuit diagram of an electrostatic chuck with a sensing electrode.

To measure the amount of charge deposited, the sensing electrode is connected in series with a capacitor of known value. For example, a 1 nF capacitor will induce 1 volt when 1 nC of charge is collected. The other pole of the known capacitor is attached to ground, and the potential across the capacitor is measured. A circuit diagram to illustrate the set-up is shown in FIG. 11. Referring to FIG. 11, $V_m$ is a high impedance voltmeter or an electrometer, C is the capacitance of a capacitor of known value, such as 1 $\mu F$, C' is the capacitance of the capacitor formed between the sensing electrode $e_s$ and the deposited charge $e_p$ resulting from the deposition of charged particles.

Without being limited to a particular theory, the following mathematical formulas can be used to evaluate the measurement of deposited charges by the sensing electrode according to the above circuit diagram.

C' is the capacitor formed by the sensing electrode and the charged particles. C is a capacitor of known value. C has a zero initial charge. When charged particles land on the sensing electrode, they cause an equal amount of opposite charge to be induced on the electrode which will subsequently induce an equal amount of opposite charge on C. The overall effect results in an equal amount and equal sign of charge induced on C, which can be measured by an electrometer. Furthermore, the dominating electrical noise associated with an active power source is removed. The collected charge Q' is equal to C times V.

With this monitoring method using the sensing electrode, two parameters need to be predetermined to monitor the amount of actual deposition. These two parameters are the q/m (charge to mass) ratio of the charged powder and the relation factor k between the monitored charge Q' and the deposited charge Q on the deposition area of interest (i.e. k=Q/Q'). Hence, the deposited mass M is determined by the equation:

$$M = \frac{Q'}{k\frac{q}{m}} 7$$

The reliability of the sensing electrode requires that the variable k is substantially constant throughout the deposition.

The use of a sensing electrode is preferred over the use of an ammeter or voltmeter within the circuit since the sensing electrode provides the advantages, for example, of correcting for collection of charges from the ambient atmosphere and other leakage paths induced by the chuck.

Preferably, the charge:mass ratio of the objects to be dispensed is measured during the deposition process to provide feedback control for termination of deposition when the desired number of objects have been deposited. For example, feedback control can be used to monitor deposition of a pharmaceutical powder until the appropriate dosage has been achieved.

Figure 17A:
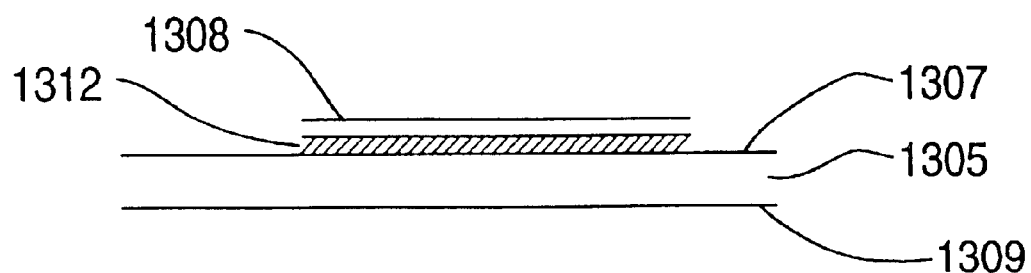
FIG. 17A is a diagrammatic cross-section of a modified quartz crystal monitor.
Figure 17B:
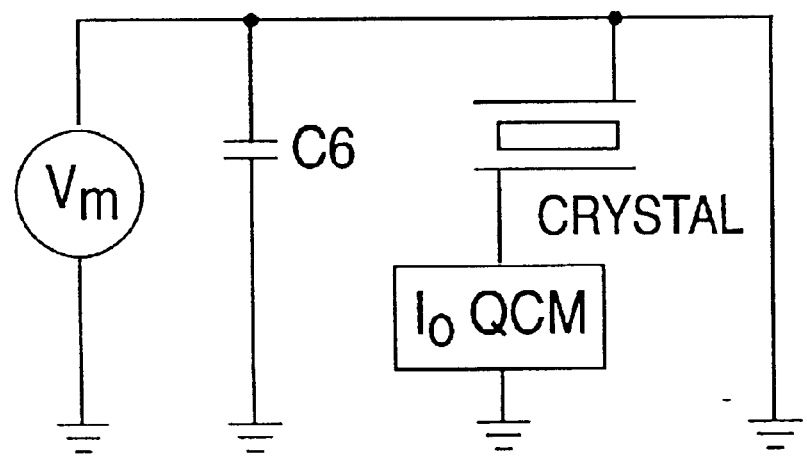
FIG. 17B is a circuit diagram of the monitor shown in FIG. 17A.

The average charge:mass ratio can be measured, for example, using a velocimeter and a modified quartz crystal monitor. Referring to FIG. 17A, the quartz crystal monitor 1305 has a top sensing layer 1307 and a bottom layer 1309 for connection to a meter. The quartz crystal monitor is modified by adding a charge sensing layer 1308, which is a second conductive layer, and a dielectric layer 1312, as illustrated in FIG. 17A. This modification causes the monitor to sense both charge and mass at the same time. See, for example, the circuit diagram of the monitor shown in FIG. 17B, in which Cs is the capacitor due to the dielectric layer, which measures the collected charge.

Preferably, at least two charge:mass monitors are used, one with the acoustic dispenser, and the other with the chuck or other means holding the recipient substrate or substrates.

Thus, in another aspect, the present invention provides a method of attracting a selected number of multiple particles to a substrate, comprising (a) providing an electrostatic chuck with a sensing electrode; (b) applying multiple electrostatically charged particles to the chuck; and (c) sensing the number of particles attracted to the chuck. Preferably, the particles are particles of a dry powder and the method is used to determine the amount of powder deposited on a substrate attracted to the chuck. The invention therefore provides a method of accurately determining the dosage in a pharmaceutical tablet.

Additionally, the invention provides a method of manufacturing a pharmaceutical composition comprising (a) providing a pharmaceutical substrate; and (b) electrostatically depositing particles on the substrate, the deposition preferably comprising the use of an electrostatic chuck. Preferably, the electrostatic chuck comprises a floating electrode and the particles are substantially deposited on an area of the substrate corresponding to the floating electrode, and the electrostatic chuck preferably further comprises a sensing electrode for determining the amount of particles deposited on the substrate.

8. Objects Created Using The Electrostatic Chucks of the Invention

The invention additionally provides objects having selected areas in which particles are applied to the object via electrostatic means, such as charge imaging. The use of electrostatic means creates a more accurate deposition of particles in a selected image, thus providing for a manner of identification of such an object. The deposition also shows greater uniformity, and provides for less waste of particles.

In preferred embodiments, the particles comprise a pharmaceutically active ingredient, and the object is suitable for human consumption, and preferably comprises a pharmaceutical substrate such as a tablet, capsule or caplet. In other preferred embodiments, the object is a suppository or it is selected from the group consisting of an inhaler substrate, a dressing, bandage and a patch. Preferably, the amount of particles applied to the object are predetermined using a sensing electrode in the electrostatic means. Additionally, in preferred embodiments, the particles are applied to the object using an acoustic dispenser described below.

The invention is further illustrated by the following non-limiting examples.

EXAMPLE 1

Electrostatic Chuck with an Upper Conductive Layer Having Two Interdigitated Electrodes An electrostatic chuck with an upper conductive layer having two interdigitated electrodes was fabricated as follows. A glass substrate was used, the substrate having an ITO (indium tin oxide) interdigitated electrode, forming an upper conductive layer less than about 25 microns thick. On top of the upper conductive layer was a thin polystyrene layer using Scotch brand tape, having about 1 mil thickness.

In one test, 1000 volts was applied across the electrodes and a tablet weighing about 65 mg and having a diameter of about 5.6 mm was held to the chuck. When 1400 volts were applied, the tablet was repelled from the chuck, possibly due to a surge resulting in a discharge due to a repulsive force.

In a second test, a tablet was placed on top of the tape and 500 V D.C. was applied to the electrodes. The chuck was turned upside down and the tablet was held in place by the chuck.

In a third test, three tablets were applied to the chuck using 500 V and the voltage was decreased until all three fell off the chuck. The first tablet fell off at 300 V, the second tablet fell off at 200 V, and the third tablet fell off at 100 V. The test results showed that the holding force is proportional to $V^2$.

In another test, six hundred volts was applied to one of the two interdigitated electrodes of the chuck, and the other electrode was grounded. One tablet was placed on the polystyrene side of the chuck, and the tablet remained on the chuck after turning the chuck upside down and subjecting the tablet to the force of gravity.

The chuck was also tested for depositing powder on a tablet while held by the chuck. Using air propulsion to deposit a positively charged steroid in a 3% suspension of beads, it was determined that at least about 47 $\mu$g was deposited.

EXAMPLE 2

Electrostatic Chuck with a Single Electrode in the Upper Conductive Layer

An electrostatic chuck having a single electrode in the upper conductive layer was configured as follows. The bottom of the chuck was a lower conductive layer made of aluminum layered onto a dielectric layer made of polyimide laminated onto copper (Good Fellows, Berwyn, Pa.). The thickness of the polyimide layer was about 2 mils. Three copper wires on top of the polyimide formed the upper conductive layer, and functioned as an electrode. The thickness of the copper layer was about 4 mils. The distance between the copper wires was about 5.6 mm. Eighty-six tablets were used, each having a diameter of about 5.6 mm and each weighing about 65 mg, and being made of about 95% cellulose and about 3% lactose, each with a thickness of about 2 mm. The tablets were adhered to the chuck for approximately five minutes, using 1500 volts applied between the upper and lower conductive layers.

A steroid drug powder was applied to the tablets held by the chuck described above as follows. A mixture of 3% drug with Kynar coated steel beads (Vertex Image Products, Yukom, Pa.) having a diameter of about 100 microns was stored in a Teflon bottle. 585.0 mg of drug powder, in a combination of drug and beads weighing 20.6354 g, was deposited on the tablets for about 6 minutes, using the acoustic dispenser described in Example 8 below at a frequency of 87 Hz, which was determined to be the optimum frequency for the dispenser. The mesh of the acoustic dispenser for separating drug powder from beads was placed at a distance of 0.5 to 1.0 inches from the tablets receiving the powder.

EXAMPLE 3

Electrostatic Chuck with Floating Electrodes

An electrostatic chuck with floating electrodes having the following configuration was tested. The lower conductive layer was made of copper tape and was about 4 mils in thickness. The next layer was a dielectric layer made of Scotch brand polystyrene tape and about 1 mil in thickness. On top of the dielectric layer was an upper conductive layer made of a standard multipurpose through hole wire wrapped board (Radioshack) and about 0.0625 inch thick, forming an electrode, with a gap between a shielding electrode and a floating electrode, which are electrically connected. The floating electrode was round, and about 2.1 mm in diameter. The shielding electrode was round, and about 2.5 mm in diameter. The gap between the shielding and the floating electrode was about 200 microns. A substrate was placed on the upper conductive layer, the substrate being a dielectric layer made of Scotch brand polystyrene tape and about 1 mil in thickness.

To use the chuck, about −1800 volts were applied to the upper conductive layer. Next, steroid drug particles were applied to the chuck using the dispenser described in Example 8.

Figure 12A:
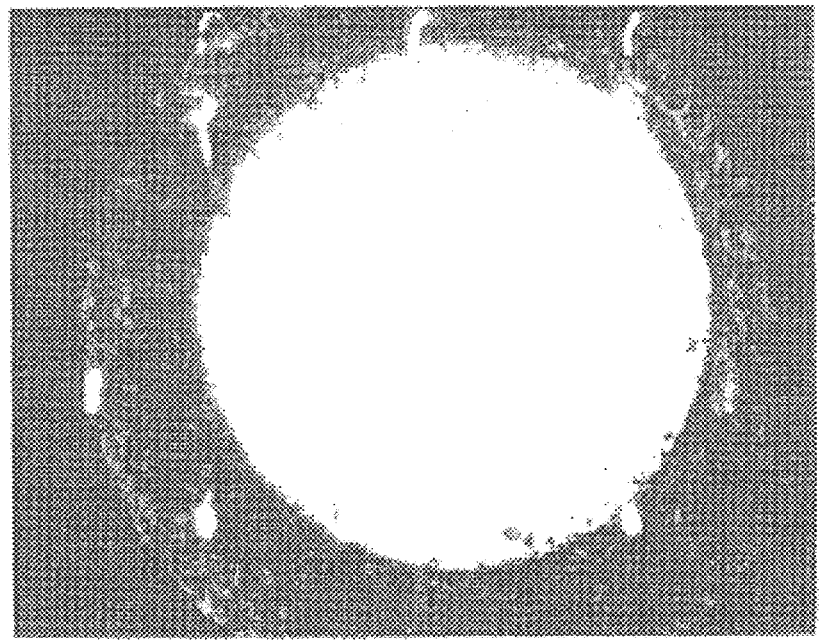
FIG. 12A is a photograph of a top view of a floating electrode after powder deposition, in a chuck without the lower conductive layer, with the printed circuit board attached. The photograph was taken at about 50× magnification; therefore, the line adjacent to the photograph represents a length of about 0.5 mm therein.
Figure 12B:
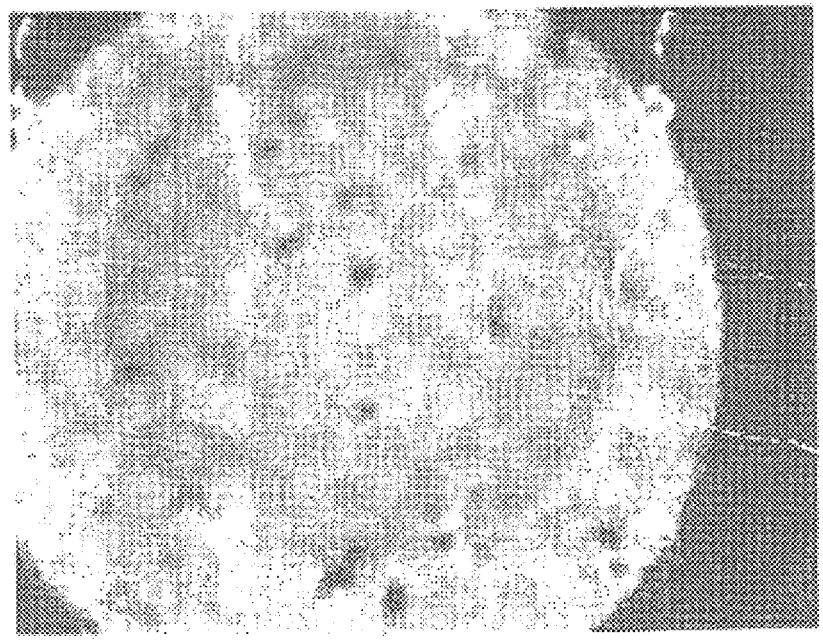
FIG. 12B is a photograph of a top view of a floating electrode after powder deposition, in a chuck with the lower conductive layer, with the printed circuit board attached. The photograph was taken at about 50×magnification; therefore, the line adjacent to the photograph represents a length of about 0.5 mm therein.
Figure 13A:
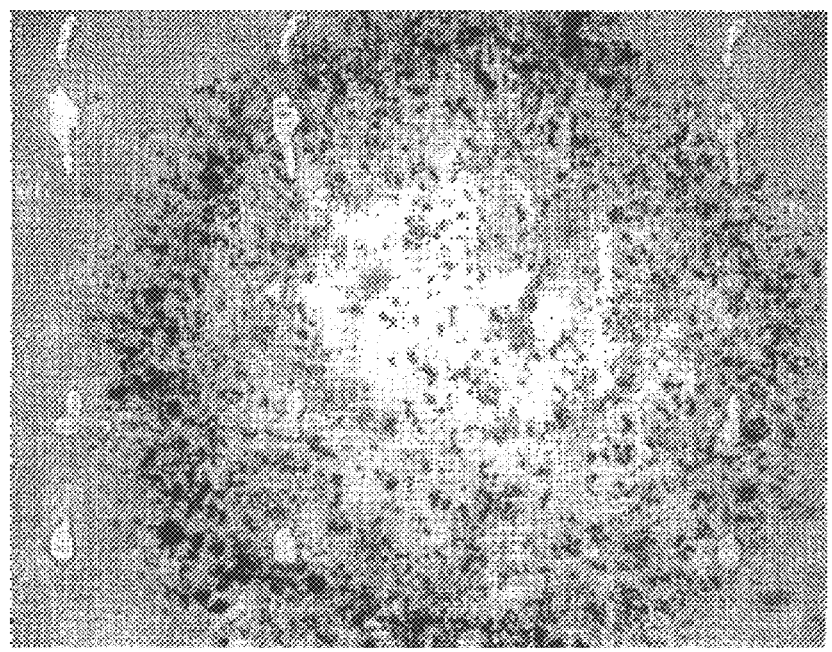
FIG. 13A is a photograph of a top view of a floating electrode after powder deposition, in a chuck without the lower conductive layer, with the printed circuit board removed. The photograph was taken at about 50×magnification; therefore, the line adjacent to the photograph represents a length of about 0.5 mm therein.
Figure 13B:
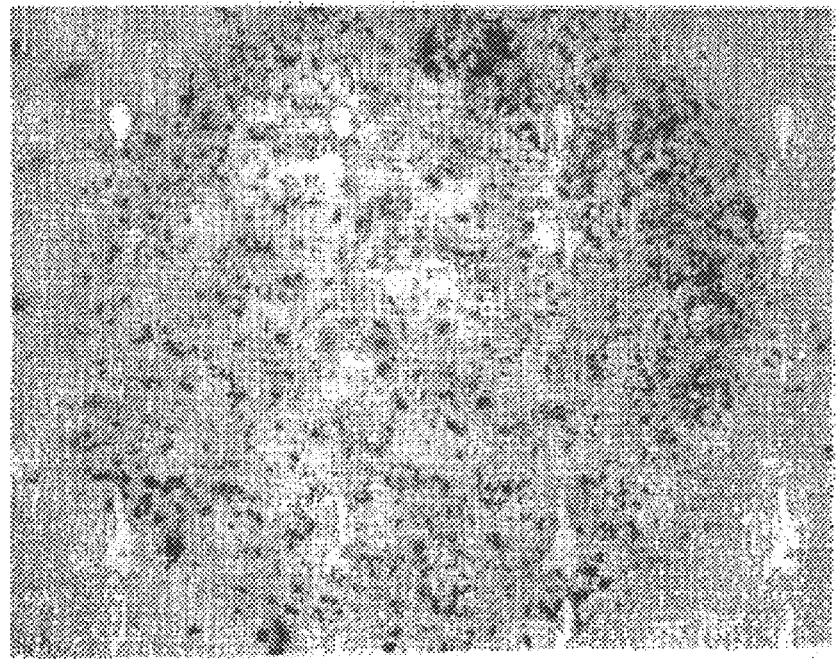
FIG. 13B is a photograph of a top view of a floating electrode after powder deposition, in a chuck with the lower conductive layer, with the printed circuit board removed. The photograph was taken at about 50×magnification; therefore, the line adjacent to the photograph represents a length of about 0.5 mm therein.
Figure 14A:
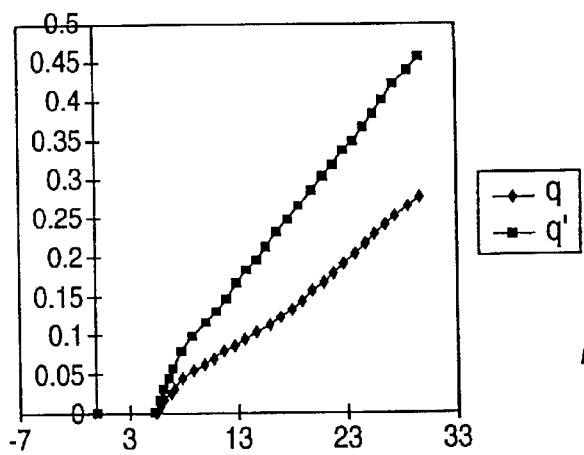
FIGS. 14A–C are graphical representations of the detection of powder deposited using a sensing electrode with an electrostatic chuck of the present invention. The x axis represents the time in minutes and the y axis represents the charge in microcoulombs. dq/dt represents the deposition rate.
Figure 14B:
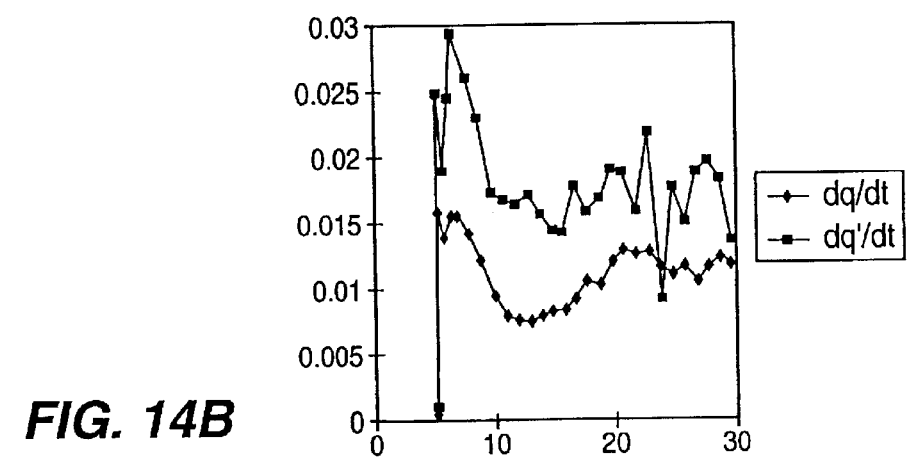

FIGS. 12–13 show the deposition of the powder on a floating electrode using a bias potential of −1800 volts with the chuck described above. The lower conductive layer, which is a printed circuit board, shows the control of the alignment of the powder during deposition. In FIGS. 12A and 13A, the lower conductive layer was omitted whereas in FIGS. 12B and 14B, it was present. FIG. 12A shows that, in the absence of the lower conductive layer, the charged particles accumulate at the edges of the floating electrode. FIGS. 12B and 13B, in contrast, show that in the presence of the lower conductive layer, the charged particles are uniformly spread throughout the floating electrode. The greatest quantity of powder deposited was found in the conditions present in FIG. 13B, in the presence of the lower conductive layer.

EXAMPLE 4

Electrostatic Chuck with Sensing Electrode

An electrostatic chuck with a sensing electrode is constructed as follows. The sensing electrode consists of a lower conductive layer made of aluminum and having on top of it a dielectric layer made of aluminum oxide. A sensing electrode is placed on the electrostatic chuck so that it is outside the recipient substrate that is subject to deposition. The sensing electrode is used to indirectly determine the amount of deposition of charged particles by measuring the change in charge before and after deposition.

Another electrostatic chuck is constructed with a sensing electrode placed on the chuck in an area within the recipient substrate, thereby causing both the sensing electrode and the recipient substrate to be subject to deposition. In this case, the sensing electrode is used to directly determine the amount of deposition of charged particles by measuring the change in charge before and after deposition.

A third electrostatic chuck is constructed with two sensing electrodes, one placed within the recipient substrate, and the other placed outside the recipient substrate. In this case, the sensing electrode within the recipient substrate is used to directly determine the amount of deposition of charged particles by measuring the change in charge before and after deposition, and is also used to calibrate the measurement of deposition by the sensing electrode outside the area of deposition.

A sensing electrode in a ring configuration was fabricated using anodized aluminum oxide (aluminum as the conductive layer forming the electrode and the oxide layer as the dielectric). 15 g of beads were used and were shaken together with a micronized steroid drug powder (cortisone, Aldrich Chemical Co., Milwaukee Wis.) for about 30 minutes. Two concentrations of powder were used, one having 450 mg of powder per 15 g beads (3% mixture) and one having 900 mg of powder for 15 g beads (6% mixture). 1800 volts were applied to the electrostatic chuck. Acoustic energy was used to propel the powder according to Example 8, using either 1400 (corresponding to about 12 Watts), 1600 or 1800. The change in charge during deposition was measured by recording the voltage on the electrometer every 30 seconds for the first two minutes and every minute thereafter until 30 minutes total had passed. The amount of powder deposited on a pre-weighed amount of aluminum foil was also measured.

Figure 14C:
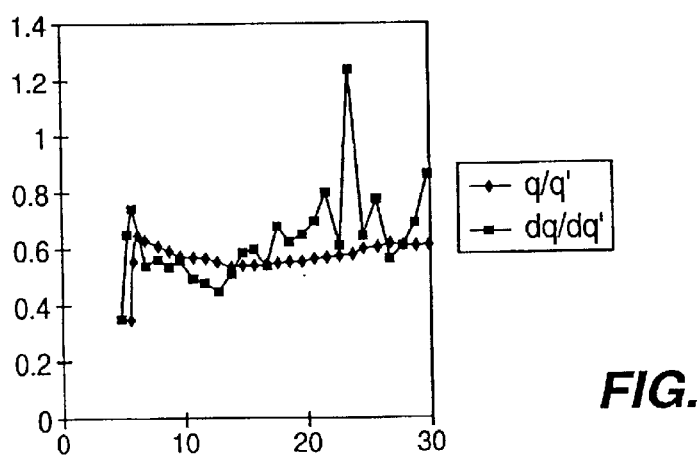

Multiple tests were undertaken by performing deposition on aluminum foil, the time for complete deposition taking about five minutes. Tests showed that with steady state deposition, k varies up to 4% in either direction. k is the ratio between the monitored charge Q' and the deposited charge Q and is actually a function of all operational parameters of the chuck and acoustic dispenser; therefore, k is determined experimentally. A k inconsistency in excess of 10% is accompanied by a change of dispenser characteristic. The data obtained in tests of the sensing electrode is provided in Tables VI and VII below, and FIGS. 14A–C, which provide a graphical representation of the experimental data using a sensing electrode in the guard ring configuration.

TABLE VI

| Time | Q | Q' | Audio Se | q | q' | dq/dt | dq'/dt | q/q' | dq/dq' | q/q' analysis | |
|---|---|---|---|---|---|---|---|---|---|---|---|
| 0 | 0.00021 | 0.00115 | 900 | 0 | 0 | | | | | average after 18 minutes | 0.58499 |
| 5 | 0.00207 | 0.00666 | 1600 | 0.00186 | 0.00551 | 0.000372 | 0.001102 | | 0.337568 | Std deviation | 0.020353 |
| 5.5 | 0.00995 | 0.0191 | 1600 | 0.00974 | 0.01795 | 0.01576 | 0.02488 | 0.337568 | 0.633441 | Relative deviation | 0.034792 |
| 6 | 0.01685 | 0.02853 | 1600 | 0.01664 | 0.02738 | 0.0138 | 0.01888 | 0.542618 | 0.731707 | average after 7 minutes | 0.569577 |
| 6.5 | 0.02458 | 0.04082 | 1600 | 0.02437 | 0.03967 | 0.01546 | 0.02458 | 0.607443 | 0.628967 | Std deviation | 0.026827 |
| 7 | 0.03238 | 0.0556 | 1600 | 0.03217 | 0.05445 | 0.0156 | 0.02956 | 0.614318 | 0.52774 | Relative deviation | 0.0471 |
| 8 | 0.04667 | 0.08163 | 1600 | 0.04646 | 0.08048 | 0.01429 | 0.02603 | 0.590817 | 0.548982 | average after 5 minutes | 0.561399 |
| 9 | 0.05885 | 0.1047 | 1600 | 0.05864 | 0.10335 | 0.01218 | 0.02307 | 0.577286 | 0.527958 | Std deviation | 0.052168 |
| 10 | 0.06836 | 0.122 | 1600 | 0.06815 | 0.12085 | 0.00951 | 0.0173 | 0.566296 | 0.549711 | Relative deviation | 0.092925 |
| 11 | 0.0764 | 0.13875 | 1600 | 0.07619 | 0.1376 | 0.00804 | 0.01675 | 0.563922 | 0.48 | | |
| 12 | 0.08408 | 0.15525 | 1600 | 0.08387 | 0.1541 | 0.00768 | 0.0165 | 0.553706 | 0.465455 | | |
| 13 | 0.09168 | 0.1725 | 1600 | 0.09147 | 0.17135 | 0.0076 | 0.01725 | 0.544257 | 0.44058 | Average over 25 minutes | 25 |
| 14 | 0.09972 | 0.1882 | 1600 | 0.09951 | 0.18705 | 0.00804 | 0.0157 | 0.53382 | 0.512102 | Deposition rate (mg/min) | 1.0056 |
| 15 | 0.10813 | 0.2028 | 1600 | 0.10792 | 0.20165 | 0.00841 | 0.0146 | 0.531997 | 0.576027 | Dep. rate (μg/min/mm2) | 0.580515 |
| 16 | 0.11658 | 0.2172 | 1600 | 0.11637 | 0.21605 | 0.00845 | 0.0144 | 0.535185 | 0.586806 | Dep. rate (μg/min/tablet) | 14.40048 |
| 17 | 0.12604 | 0.235 | 1600 | 0.12583 | 0.23385 | 0.00946 | 0.0178 | 0.538625 | 0.531461 | Time for 35 μg (low dose) | 2.430474 |
| 18 | 0.13679 | 0.251 | 1600 | 0.13658 | 0.24985 | 0.01075 | 0.016 | 0.53808 | 0.671875 | Time for 250 μg (high dose) | 17.36053 |
| 19 | 0.14727 | 0.268 | 1600 | 0.14706 | 0.26685 | 0.01048 | 0.017 | 0.546648 | 0.616471 | q/m (μC/g) | 11.79282 |
| 20 | 0.15943 | 0.2871 | 1600 | 0.15922 | 0.28595 | 0.01216 | 0.0191 | 0.551096 | 0.636649 | | |
| 21 | 0.17248 | 0.306 | 1600 | 0.17227 | 0.30485 | 0.01305 | 0.0189 | 0.556811 | 0.690476 | Average last 5 minutes | 5 |
| 22 | 0.18518 | 0.322 | 1600 | 0.18497 | 0.32085 | 0.0127 | 0.016 | 0.565098 | 0.79375 | Deposition rate (mg/min) | 1.054461 |
| 23 | 0.19811 | 0.3438 | 1600 | 0.1979 | 0.34265 | 0.01293 | 0.0218 | 0.5765 | 0.593119 | Dep. rate (μg/min/mm2) | 0.608722 |
| 24 | 0.2099 | 0.3533 | 1600 | 0.20969 | 0.35215 | 0.01179 | 0.0095 | 0.577557 | 1.241053 | Dep. rate (μg/min/tablet) | 15.10019 |
| 25 | 0.2212 | 0.371 | 1600 | 0.22099 | 0.36985 | 0.0113 | 0.0177 | 0.595456 | 0.638418 | Time for 35 μg (low dose) | 2.317852 |
| 26 | 0.233 | 0.3863 | 1600 | 0.23279 | 0.38515 | 0.0118 | 0.0153 | 0.597513 | 0.771242 | Time for 250 μg (high dose) | 16.55609 |
| 27 | 0.2437 | 0.4053 | 1600 | 0.24349 | 0.40415 | 0.0107 | 0.019 | 0.604414 | 0.563158 | | |
| 28 | 0.2555 | 0.425 | 1600 | 0.25529 | 0.42385 | 0.0118 | 0.0197 | 0.602474 | 0.598985 | | |
| 29 | 0.268 | 0.4433 | 1600 | 0.26779 | 0.44215 | 0.0125 | 0.0183 | 0.602312 | 0.68306 | | |
| 30 | 0.2799 | 0.4571 | 1600 | 0.27969 | 0.45595 | 0.0119 | 0.0138 | 0.605654 | 0.862319 | | |

TABLE VII

| dq/dq' analysis | |
|---|---|
| average after 18 minutes | 0.733839 |
| Std deviation | 0.192065 |
| Relative deviation | 0.261727 |
| average after 7 minuts | 0.629475 |
| Std deviation | 0.16644 |
| Relative deviation | 0.264411 |
| average after 5 minutes | 0.633389 |
| Std deviation | 0.157774 |
| Relative deviation | 0.249094 |
| Foil mass before deposition | 160.86 |
| Foil mass after deposition | 186 |
| Mass gain | 25.14 |
| Length (in) | 1.79 |
| Width (in) | 1.5 |
| Area (in2) | 2.685 |
| Area (mm2) | 1732.255 |
| Tablet diameter (mm) | 5.62 |
| Tablet diameter (mm2) | 24.80639 |
| Capacitor value (μF) | 1.06 |

What is claimed is:

1. A tablet, film, capsule, caplet, suppository, dressing, bandage or patch manufactured by steps comprising:

(a) adhering a pharmaceutical substrate to an electrostatic chuck;

(b) applying particles of medicament essentially free of excipients to the pharmaceutical substrate which is adhered to the electrostatic chuck, and electrostatically adhering the particles to the substrate to form a layer of medicament essentially free of excipients; and (c) forming the tablet, film, capsule, caplet, suppository, dressing, bandage or patch comprising the substrate and layer of medicament essentially free of excipients.

2. The tablet, film, capsule, caplet, suppository, dressing, bandage or patch of claim 1, wherein the medicament is a steroid.

3. The tablet, film, capsule, caplet, suppository, dressing, bandage or patch of claim 1, wherein the medicament is a cortisone.

4. The tablet, film, capsule, caplet, suppository, dressing, bandage or patch of claim 1, wherein the particles are of 1 micron to 10 micron diameter.

5. The tablet of one of claims 1–3.

6. The film of one of claims 1–3.

7. The capsule of one of claims 1–3.

8. The caplet of one of claims 1–3.

9. The suppository of one of claims 1–3.

10. The dressing of one of claims 1–3.

11. The bandage of one of claims 1–3.

12. The patch of one of claims 1–3.

* * * * *